(12) United States Patent
Mo et al.

(10) Patent No.: US 11,365,207 B2
(45) Date of Patent: Jun. 21, 2022

(54) SULFUR-CONTAINING POLYCYCLIC-HYDROXYPYRIDONE CARBOXAMIDE ANALOG AGAINST HIV

(71) Applicant: Yunfen Mo, Shanghai (CN)

(72) Inventors: Yunfen Mo, Shanghai (CN); Cuiwu Lin, Shanghai (CN); Anran Zhao, Shanghai (CN)

(73) Assignee: Yunfen Mo, Shanghai (CN)

( * ) Notice: Subject to any disclaimer, the term of this patent is extended or adjusted under 35 U.S.C. 154(b) by 0 days.

(21) Appl. No.: 16/987,402

(22) Filed: Aug. 7, 2020

(65) Prior Publication Data

US 2020/0361960 A1    Nov. 19, 2020

Related U.S. Application Data

(63) Continuation of application No. PCT/CN2019/078571, filed on Mar. 18, 2019.

(30) Foreign Application Priority Data

May 23, 2018 (CN) .......................... 201810502584.0

(51) Int. Cl.
| | | |
|---|---|---|
| *C07D 513/14* | (2006.01) |
| *C07D 513/16* | (2006.01) |
| *A61K 31/4985* | (2006.01) |
| *A61K 31/4995* | (2006.01) |
| *A61K 31/542* | (2006.01) |
| *A61K 31/547* | (2006.01) |
| *A61K 31/554* | (2006.01) |
| *A61P 31/18* | (2006.01) |

(52) U.S. Cl.
CPC ............ *C07D 513/14* (2013.01); *A61P 31/18* (2018.01)

(58) Field of Classification Search
CPC .. C07D 513/14; C07D 513/15; C07D 513/16; A61K 31/4985; A61K 31/4995; A61K 31/542; A61K 31/547; A61K 31/554; A61K 45/06; A61P 31/18
See application file for complete search history.

(56) References Cited

U.S. PATENT DOCUMENTS

| 9,216,996 B2 | 12/2015 | Jin et al. |
| 2015/0018359 A1 | 1/2015 | Desai et al. |
| 2016/0207939 A1 | 7/2016 | Johns et al. |

FOREIGN PATENT DOCUMENTS

| CN | 104876950 A | 9/2015 |
| EP | 3196201 A1 | 7/2017 |

OTHER PUBLICATIONS

Internation Search Report of PCT/CN2019/078571, dated Jun. 5, 2019.

*Primary Examiner* — Bruck Kifle

(57) ABSTRACT

The disclosure discloses a sulfur-containing polycyclic-hydroxypyridone carboxamide analog against HIV and an application thereof. The sulfur-containing polycyclic-hydroxypyridone carboxamide analog has a compound represented by the following formula (I) or a stereoisomer thereof or a pharmaceutically acceptable salt thereof. The sulfur-containing polycyclic-hydroxypyridone carboxamide analogs provided by the disclosure have good anti-HIV activity, and in particularly, compound 2, compound 18, compound 34 and compound 66 have strong inhibitory effects on HIV-1 replication in vitro, and the therapeutic index thereof against HIV is hundreds of times greater than that of the existing drugs TDF and Dolutegravir. The development of such the compounds is of great significance for the development of AIDS drugs and will bright good news to AIDS patients.

14 Claims, No Drawings

SULFUR-CONTAINING POLYCYCLIC-HYDROXYPYRIDONE CARBOXAMIDE ANALOG AGAINST HIV

CROSS-REFERENCE TO RELATED APPLICATIONS

This application is a continuation of International Patent Application No. PCT/CN2019/078571 with a filing date of Mar. 18, 2019, designating the United States, and further claims priority to Chinese Patent Application No. 201810502584.0 with a filing date of May 23, 2018. The content of the aforementioned applications, including any intervening amendments thereto, are incorporated herein by reference.

TECHNICAL FIELD

The disclosure relates to the technical field of antiviral drugs, and particularly to a sulfur-containing polycyclic-hydroxypyridone carboxamide analog having anti-HIV activity and an application thereof.

BACKGROUND OF THE PRESENT INVENTION

Since the first AIDS patient has been found in the United States in 1981, this infectious disease starts to perplex human civilization. Coexistence of viruses and human beings is a struggle for each other's survival because invaders can kill people, but they are also destroying their own hosts. Organisms utilize their immune systems to protect themselves from immune deficiency diseases generated when bacteria, viruses and others fail to cause diseases. Such the disease is called acquired immune deficiency syndrome (AIDS), and is the most common outcome generated after being infected by human immunodeficiency virus (HIV). Two types of HIV, HIV-1 and HIV-2 closely related to each other, have been identified once. However, HIV-2 is spread in India and West Africa, and HIV-1 is more mortal and is a cause of the first AIDS in the world. Some patients have different outcomes, but in most cases, HIV infectors can continue to be developed into AIDS and finally die from opportunistic infection or cancers.

The human immunodeficiency virus (HIV) is a revere transcriptase virus which can cause acquired immune deficiency syndrome (AIDS). Therapeutic agents for AIDS are mainly selected from a group of reverse transcriptase inhibitors (such as AZT, 3TC and abacavir) and protease inhibitors (such as Indinavir and Amprenavir), but they are confirmed to accompany side effects, such as nephropathy and occurrence of anti-drug viruses. Therefore, it is desired to develop anti-HIV drugs having other action mechanisms.

In addition, it is reported that combination therapy can effectively treat AIDS due to frequency occurrence of a drug-resistant mutant. The reverse transcriptase inhibitors and the protease inhibitors are clinically used as anti-HIV drugs, however, drugs having the same action mechanism often show cross resistance. Therefore, there is a need for anti-HIV drugs having other action mechanisms.

Under the above conditions, development of HIV integrase inhibitors focuses on anti-HIV drugs having a new action mechanism. Integration is crucial to gene expression and virus replication of reverse viral genomes. The viral genome is reversely transcripted to DNA of infected cells by virus reverse transcriptase and then integrated to host cell chromosomes by virtue of virus integrase DNA. RNA transcription is generated from the integrated viral DNA, and the synthesis of viral proteins is guided by mRNAs and then used as RNA genomes of new virus particles. Plasma membranes escape from cells through blastogenesis virus particles and are each sealed in membrane envelopes. In this process, the HIV-1 integrase is important and thus a promising target for design of anti-AIDS drugs.

It has been found that integrase inhibitors are mutated to form over 60 mutations causing in-vivo and in-vitro drug resistance. These inhibitors generating mutations and drug resistance can effectively reduce viruses [Drug resistance updates 2010, 13(4-5), 139-150]. The drug resistance of the integrase inhibitor is equivalent to those of other anti-retroviral drugs. First, the drug resistance of the integrase is caused through a combination of major mutations that reduce the sensitivity of the integrase inhibitors and secondary mutations that further reduce the sensitivity of viruses and/or reduce the proper repair of viruses. Second, the drug resistance of the integrase inhibitor has a genetic barrier, which is defined as the number of mutations required for losing the activity of the clinical integrase inhibitor. Third, there is a wide but incomplete cross resistance in the integrase inhibitors [The Journal of infectious diseases 2011, 203 (9), 1201-1214]. A ring contains 140-149 amino acid residues and is positioned in the structure region of the catalytic core, and is important to the function of the integrase as describe above. This ring is flexible and even is considered to be important despite its action is not extremely known, and its function is crucial to DNA combination. The drug resistance appears to mutate in this integrase-encoding region [Drug resistance updates 2010, 13(4-5), 139-150]. The resistance to latiravir and elvitegravir is mainly because of two identical mutation routines, but each of drugs also involves other primary mutations [Clinical therapeutics 2008, 30 (10), 1747-1765]. Since the drug resistance problem has been present in latiravir and elvitegravir, development of a new generation of integrase inhibitors is still an important research direction. Among them, a polycyclic-hydroxypyridinone methylamide derivative is a novel compound having antiviral activity, such as Dolutegravir (patent WO2006/116764) and Bictegravir (patent WO2014/100323). At present, Dolutegravir that has been listed still has the drug resistance problem, and thus development of novel anti-HIV drugs is of great significance.

SUMMARY OF PRESENT INVENTION

The objective of the disclosure is to provide a sulfur-containing polycyclic-hydroxypyridone carboxamide analog having anti-HIV activity and an application thereof.

In order to achieve the above objective, the disclosure adopts the following technical solution:

A sulfur-containing polycyclic-hydroxypyridone carboxamide analog having anti-HIV activity, comprising a com pound represented by the following formula (I) or a stereoisomer thereof or a pharmaceutically acceptable salt thereof:

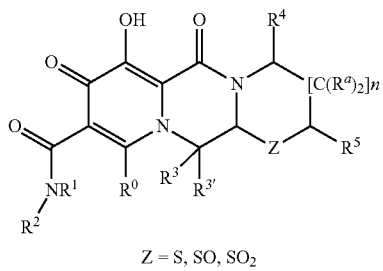

wherein, Z is selected from S, SO and $SO_2$;

$R^0$ is hydrogen, halogen, hydroxyl, optionally substituted lower alkyl or optionally substituted lower alkenyl, each of which is inserted by heteroatom groups selected from $OR^6$, $SR^6$, $SOR^6$, $SO_2R^6$ and $NR^6$; $R^6$ is hydrogen, optionally substituted lower alkyl, optionally substituted cycloalkyl, optionally substituted cycloalkyl lower alkyl, optionally substituted lower alkenyl, optionally substituted lower alkoxy, optionally substituted aryl, optionally substituted aryl lower alkyl, optionally substituted aryloxy, optionally substituted heterocyclyl, optionally substituted heterocyclic lower alkyl, optionally substituted heteroepoxy group, hydroxyl, optional amino and optionally substituted phosphate group;

Each $R^a$ is independently hydrogen, halogen, optionally substituted lower alkyl, optionally substituted cycloalkyl, optionally substituted cycloalkyl lower alkyl, optionally substituted lower alkenyl, optionally substituted lower alkoxy, optionally substituted aryl, optionally substituted aryl lower alkyl, optionally substituted aryloxy, optionally substituted heterocyclyl, optionally substituted heterocyclic lower alkyl and optionally substituted heteroepoxy group;

n is an integer of 0~8; when n is 0, the ring is a five-membered ring;

$R^1$ is hydrogen, optionally substituted lower alkyl, optionally substituted cycloalkyl, optionally substituted cycloalkyl lower alkyl, optionally substituted lower alkenyl, optionally substituted lower alkoxy, optionally substituted aryl, optionally substituted aryl lower alkyl, optionally substituted aryloxy, optionally substituted heterocyclyl, optionally substituted heterocyclic lower alkyl and optionally substituted heteroepoxy group;

$R^2$ is hydrogen, optionally substituted lower alkyl, optionally substituted cycloalkyl, optionally substituted cycloalkyl lower alkyl, optionally substituted lower alkenyl, optionally substituted lower alkoxy, optionally substituted aryl, optionally substituted aryl lower alkyl, optionally substituted aryloxy, optionally substituted heterocyclyl, optionally substituted heterocyclic lower alkyl and optionally substituted heteroepoxy group;

$R^3$ and $R^{3'}$ are independently hydrogen, optionally substituted lower alkyl, optionally substituted cycloalkyl, optionally substituted cycloalkyl lower alkyl, optionally substituted lower alkenyl, optionally substituted lower alkoxy, optionally substituted aryl, optionally substituted aryl lower alkyl, optionally substituted aryloxy, optionally substituted heterocyclyl, optionally substituted heterocyclic lower alkyl, optionally substituted heteroepoxy group, hydroxyl, optional amino and optionally substituted phosphate group;

$R^4$ and $R^5$ are each independently hydrogen, or optionally substituted lower alkyl, optionally substituted cycloalkyl, optionally substituted cycloalkyl lower alkyl, optionally substituted lower alkenyl, optionally substituted lower alkoxy, optionally substituted aryl, optionally substituted aryl lower alkyl, optionally substituted aryloxy, optionally substituted heterocyclyl, optionally substituted heterocyclic lower alkyl and optionally substituted heterocycle;

or wherein $R^4$ and $R^5$ are combined together to form —W—, wherein W is $[C(R^b)_2]_L$ (L is an integer of 1~4);

each $R^b$ is independently hydrogen, halogen, optionally substituted lower alkyl, optionally substituted cycloalkyl, optionally substituted cycloalkyl lower alkyl, optionally substituted lower alkenyl, optionally substituted lower alkoxy, optionally substituted aryl, optionally substituted aryl lower alkyl, optionally substituted aryloxy, optionally substituted heterocyclyl, optionally substituted heterocyclic lower alkyl and optionally substituted heteroepoxy group.

Preferably, a sulfur-containing polycyclic-hydroxypyridone carboxamide analog having anti-HIV activity, comprising a compound represented by the following formula (I-A) or a stereoisomer thereof or a pharmaceutically acceptable salt thereof:

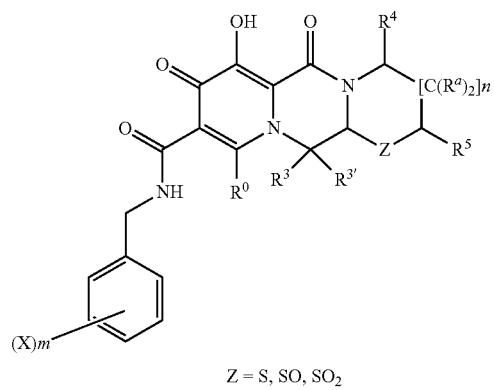

wherein, Z is selected from S, SO and $SO_2$;

$R^0$, $R^a$, n, $R^3$, $R^{3'}$, $R^4$ and $R^5$ are each selected as described above;

each X is independently hydrogen, halogen, hydroxyl, optionally substituted lower alkyl, optionally substituted cycloalkyl, optionally substituted cycloalkyl lower alkyl, optionally substituted lower alkenyl, optionally substituted lower alkoxy, optionally substituted aryl, optionally substituted aryl lower alkyl, optionally substituted aryloxy, optionally substituted heterocyclyl, optionally substituted heterocyclic lower alkyl, optionally substituted heteroepoxy group, hydroxyl, optional amino and optionally substituted phosphate group;

m is an integer of 0~3, preferably 1~3;

when m is 1, X is preferably halogen; more preferably, fluoro in the 2-position or the 4-position of the benzene ring;

when m is 2, X is preferably halogen; more preferably, fluoro in the 2-position and the 4-position of the benzene ring, fluoro in the 2-position and the 3-position of the benzene ring, fluoro in the 2-position and the 6-position of the benzene ring, fluoro in the 3-position and the 4-position of the benzene ring, fluoro in the 3-position and chloro in the 4-position of the benzene ring, fluoro in the 2-position and chloro in the 4-position of the benzene ring, or chloro in the 2-position and fluoro in the 4-position of the benzene ring; most preferably, fluoro in the 2-position and 4-position of the benzene ring;

when m is 3, X is preferably halogen; more preferably, fluoro in the 2-position, 4-position and 6-position or 2-position, 3-position and 4-position of the benzene ring, and most preferably, fluoro in the 2-position, 4-position and 6-position of the benzene ring.

Preferably, a sulfur-containing polycyclic-hydroxypyridone carboxamide analog having anti-HIV activity, comprising a compound represented by the following formula (I-B) or a stereoisomer thereof or a pharmaceutically acceptable salt thereof:

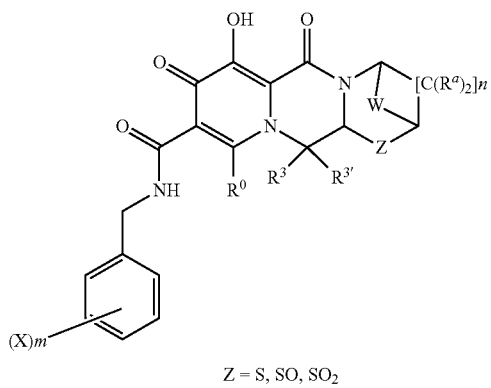

Z = S, SO, SO$_2$ wherein, Z is selected from S, SO and SO$_2$;

wherein, $R^0$, $R^a$, n, $R^3$ and $R^{3'}$ are each selected as described above;

W is $[C(R^b)_2]_L$ (L is an integer of 1~4);

each $R^b$ is independently hydrogen, halogen, optionally substituted lower alkyl, optionally substituted cycloalkyl, optionally substituted cycloalkyl lower alkyl, optionally substituted lower alkenyl, optionally substituted lower alkoxy, optionally substituted aryl, optionally substituted aryl lower alkyl, optionally substituted aryloxy, optionally substituted heterocyclyl, optionally substituted heterocyclic lower alkyl and optionally substituted heteroepoxy group;

each X is independently hydrogen, halogen, hydroxyl, optionally substituted lower alkyl, optionally substituted cycloalkyl, optionally substituted cycloalkyl lower alkyl, optionally substituted lower alkenyl, optionally substituted lower alkoxy, optionally substituted aryl, optionally substituted aryl lower alkyl, optionally substituted aryloxy, optionally substituted heterocyclyl, optionally substituted heterocyclic lower alkyl, optionally substituted heteroepoxy group, hydroxyl, optional amino and optionally substituted phosphate group;

m is an integer of 0~3, preferably 1~3;

when m is 1, X is preferably halogen; more preferably, fluoro in the 2-position or 4-position of the benzene ring;

when m is 2, X is preferably halogen; more preferably, fluoro in the 2-position and the 4-position of the benzene ring, fluoro in the 2-position and the 3-position of the benzene ring, fluoro in the 2-position and the 6-position of the benzene ring, fluoro in the 3-position and the 4-position of the benzene ring, fluoro in the 3-position and chloro in the 4-position of the benzene ring, fluoro in the 2-position and chloro in the 4-position of the benzene ring, or chloro in the 2-position and fluoro in the 4-position of the benzene ring; most preferably, fluoro in the 2-position and the 4-position of the benzene ring;

when m is 3, X is preferably halogen; more preferably, fluoro in the 2-position, 4-position and 6-position or the 2-position, 3-position and 4-position of the benzene ring, and most preferably, fluoro in the 2-position, 4-position and 6-position of the benzene ring.

Preferably, a sulfur-containing polycyclic-hydroxypyridone carboxamide analog having anti-HIV activity, comprising a compound represented by the following formula (I-C) or a stereoisomer thereof or a pharmaceutically acceptable salt thereof:

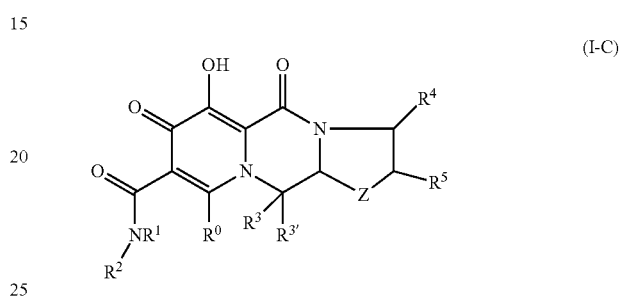

wherein, Z is selected from S, SO and SO$_2$;

$R^0$, $R^1$, $R^2$, $R^3$, $R^{3'}$, $R^4$ and $R^5$ are each selected as described above.

Preferably, a sulfur-containing polycyclic-hydroxypyridone carboxamide analog having anti-HIV activity, comprising a compound represented by the following formula (I-D) or a stereoisomer thereof or a pharmaceutically acceptable salt thereof:

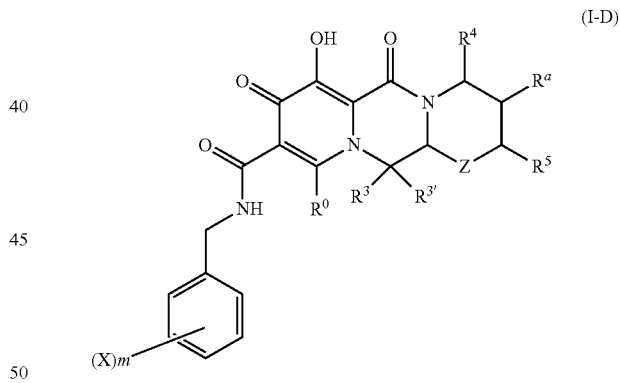

wherein, Z is selected from S, SO and SO$_2$;

$R^0$, $R^3$, $R^{3'}$, $R^a$, $R^4$ and $R^5$ are each selected as described above;

each X is independently hydrogen, halogen, hydroxyl, optionally substituted lower alkyl, optionally substituted cycloalkyl, optionally substituted cycloalkyl lower alkyl, optionally substituted lower alkenyl, optionally substituted lower alkoxy, optionally substituted aryl, optionally substituted aryl lower alkyl, optionally substituted aryloxy, optionally substituted heterocyclyl, optionally substituted heterocyclic lower alkyl, optionally substituted heteroepoxy group, hydroxyl, optional amino and optionally substituted phosphate group;

m is an integer of 0~3, preferably 1~3;

when m is 1, X is preferably halogen; more preferably, fluoro in the 2-position or 4-position of the benzene ring;

when m is 2, X is preferably halogen; more preferably, fluoro in the 2-position and the 4-position of the benzene ring, fluoro in the 2-position and the 3-position of the benzene ring, fluoro in the 2-position and the 6-position of the benzene ring, fluoro in the 3-position and the 4-position of the benzene ring, fluoro in the 3-position and chloro in the 4-position of the benzene ring, fluoro in the 2-position and chloro in the 4-position of the benzene ring, or chloro in the 2-position and fluoro in the 4-position of the benzene ring; most preferably, fluoro in the 2-position and 4-position of the benzene ring;

when m is 3, X is preferably halogen; more preferably, fluoro in the 2-position, 4-position and 6-position or 2-position, 3-position and 4-position of the benzene ring, and most preferably, fluoro in the 2-position, 4-position and 6-position of the benzene ring.

Preferably, a sulfur-containing polycyclic-hydroxypyridone carboxamide analog having anti-HIV activity, comprising a structure of compound A3 or compound A6 or compound A7, or a stereoisomer of the compound or a pharmaceutically acceptable salt thereof:

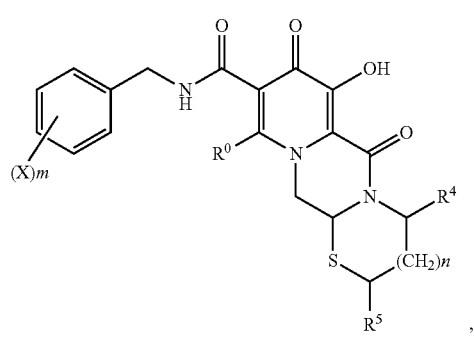

A3

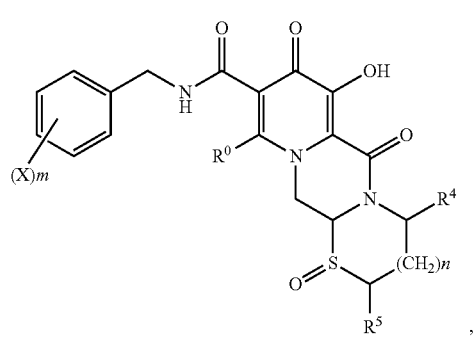

A6

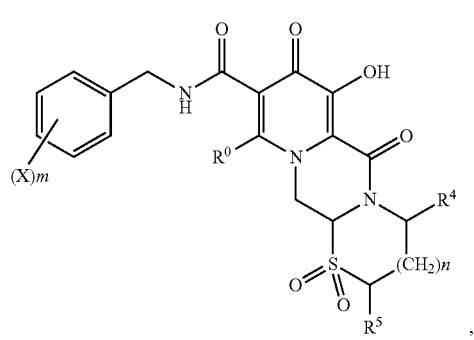

A7

Preferably, a sulfur-containing polycyclic-hydroxypyridone carboxamide analog having anti-HIV activity, which is structurally a compound whose serial number is 1-93 or enantiomers thereof; diastereomers thereof; or a mixture of diastereomers thereof; or a mixture of diastereomers thereof; or a mixture of enantiomers and diastereomers thereof; or a pharmaceutically acceptable salt thereof;

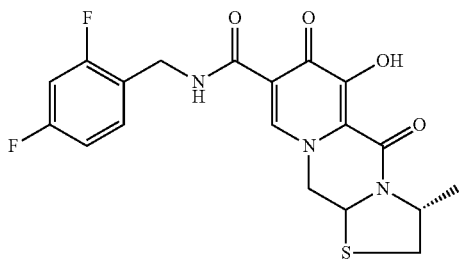

1

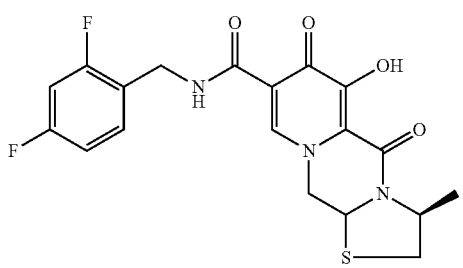

2

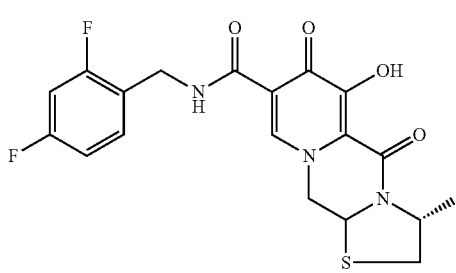

3

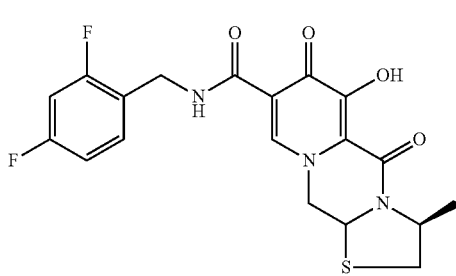

4

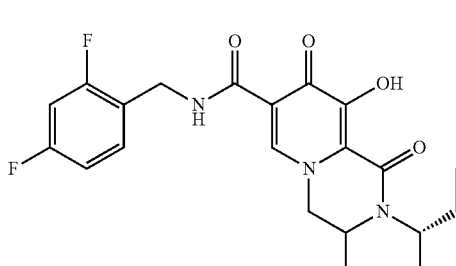

5

9
-continued
6
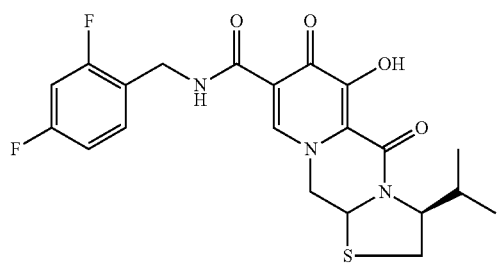
7
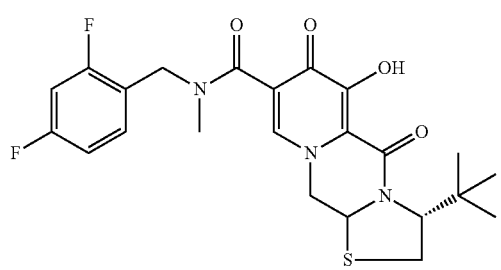
8
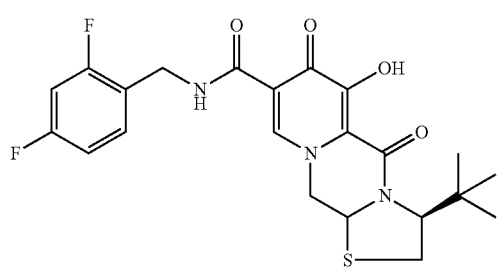
9
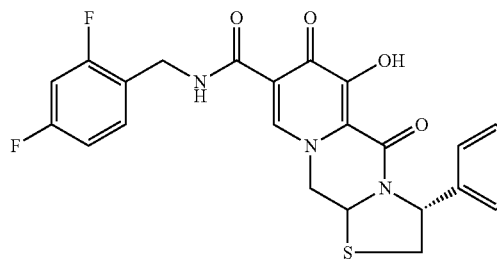
10
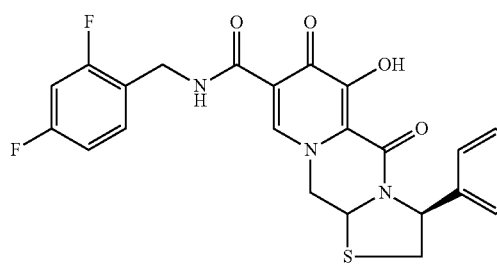
10
-continued
11
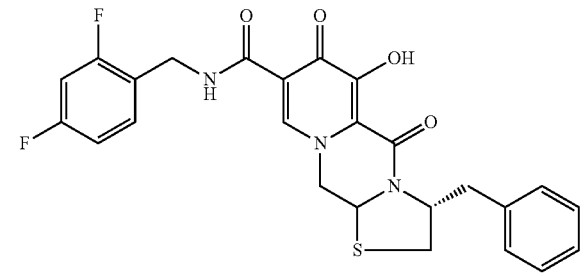
12
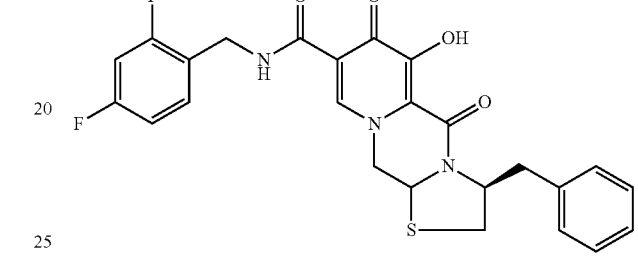
13
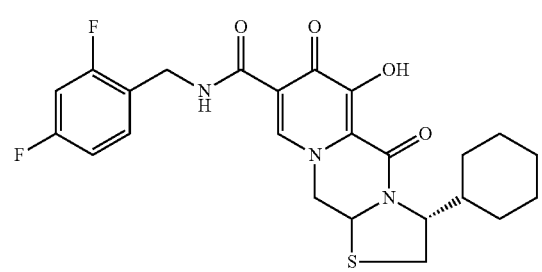
14
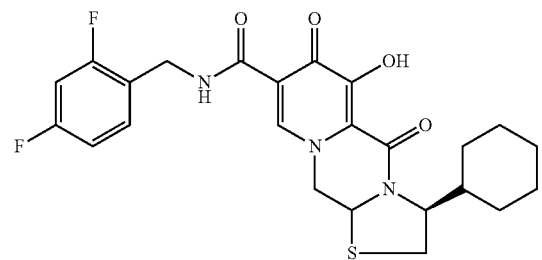
15
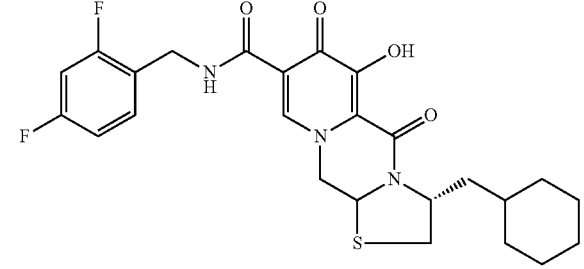

16
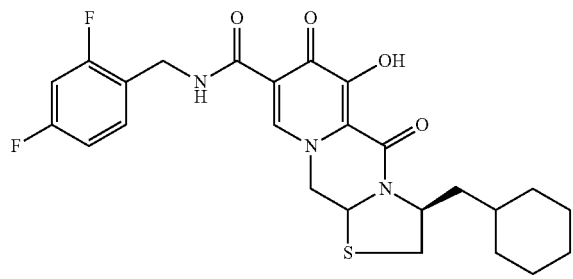
17
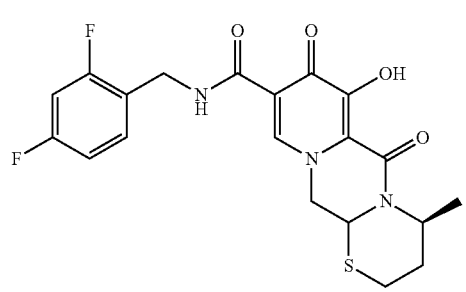
18
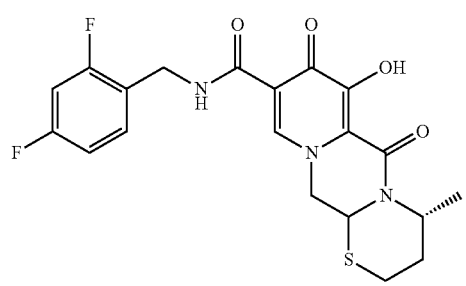
19
21
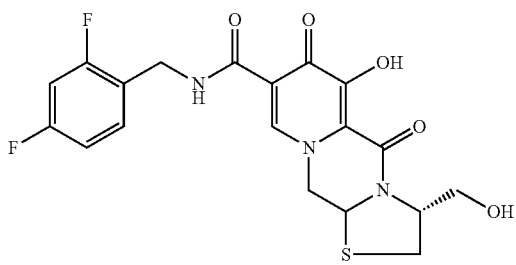
22
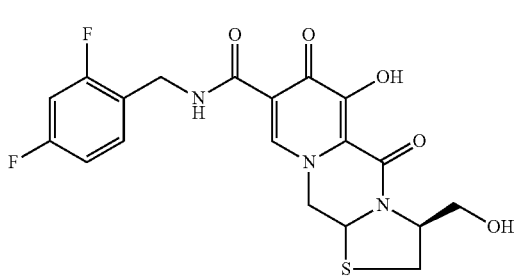
23
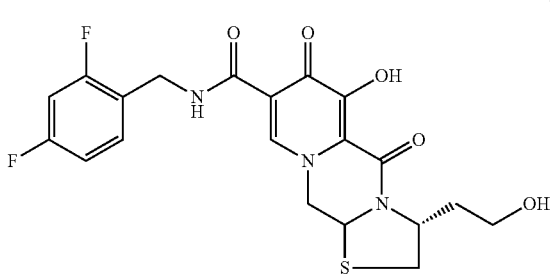
24
25

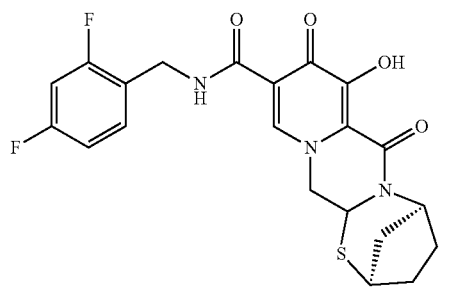
26
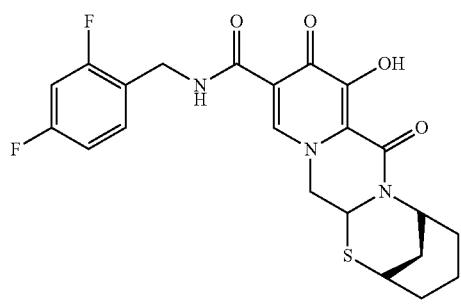
27
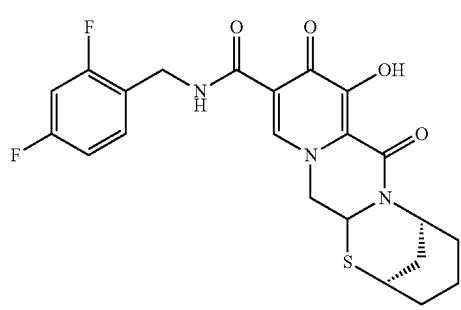
28
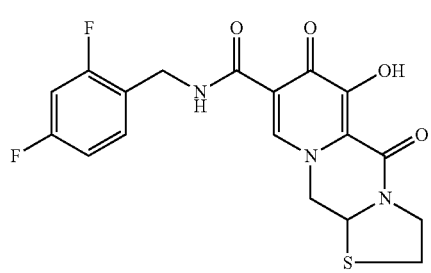
29
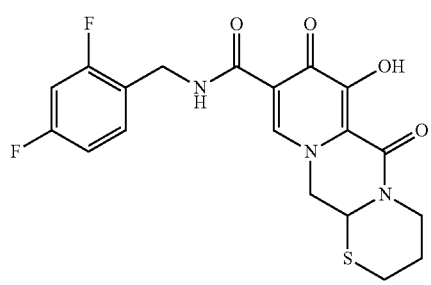
30
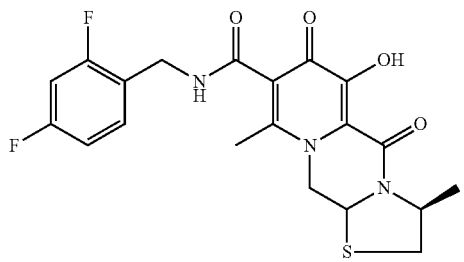
31
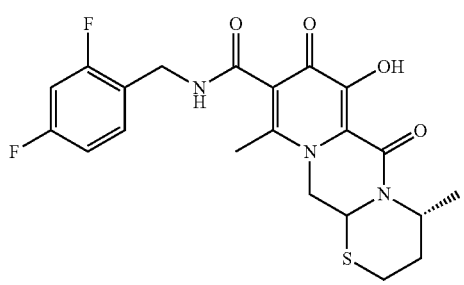
32
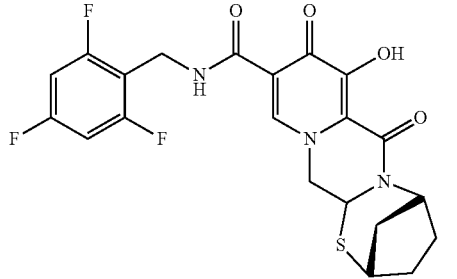
33
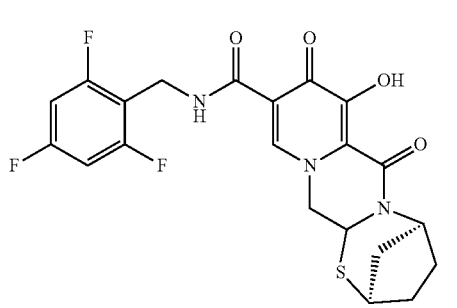
34
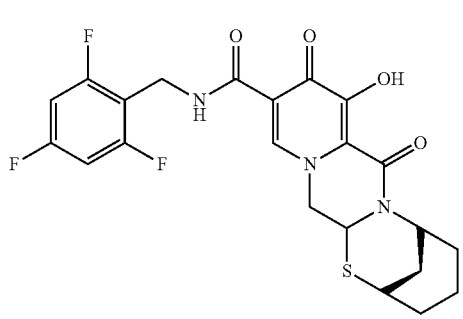
35

36
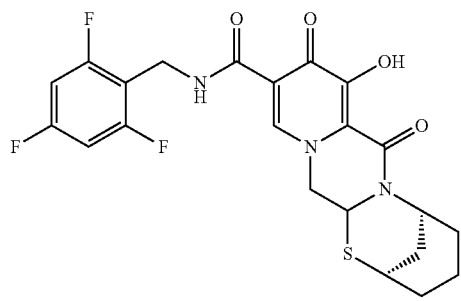
37
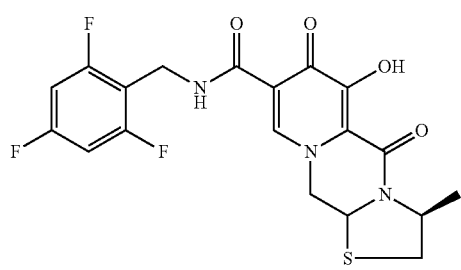
38
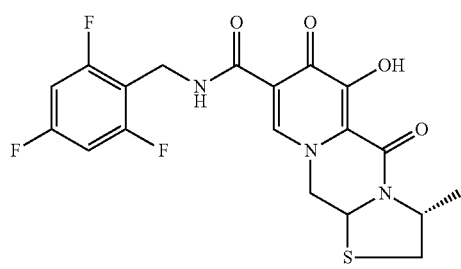
39
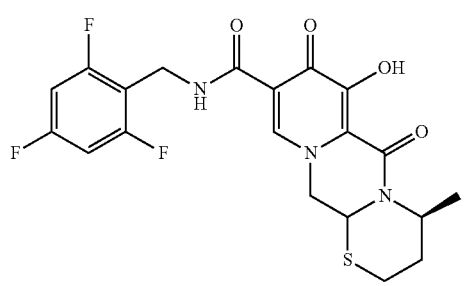
40
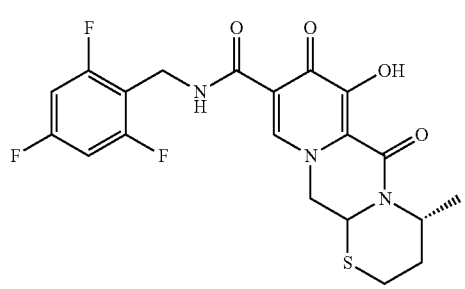
41
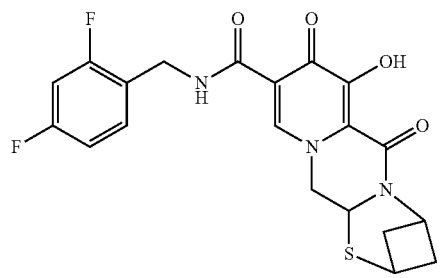
42
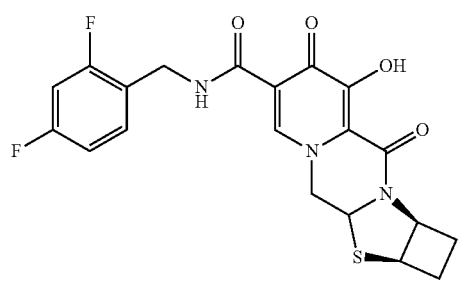
43
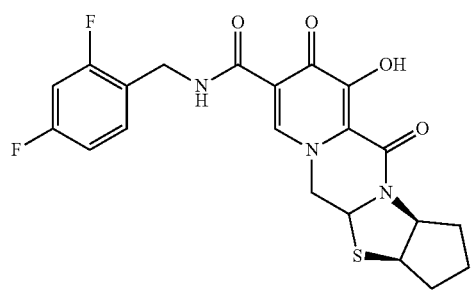
44
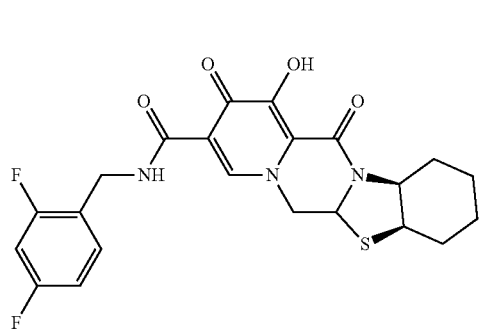
45
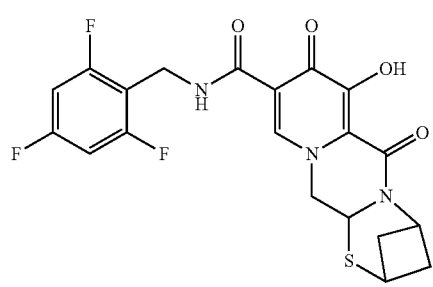

46
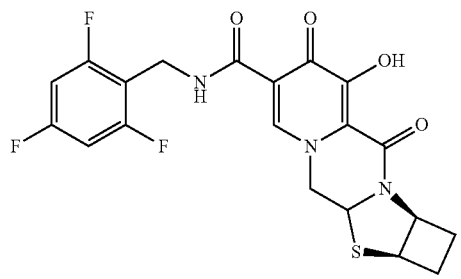
47
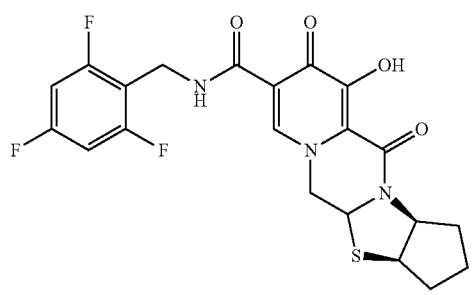
48
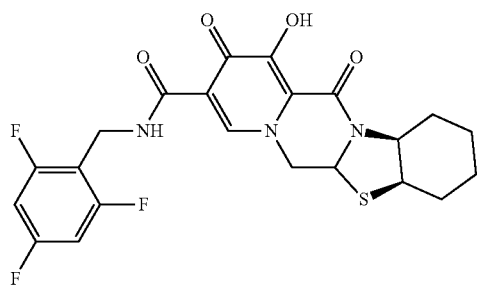
49
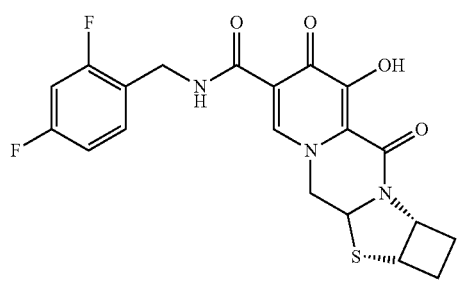
50
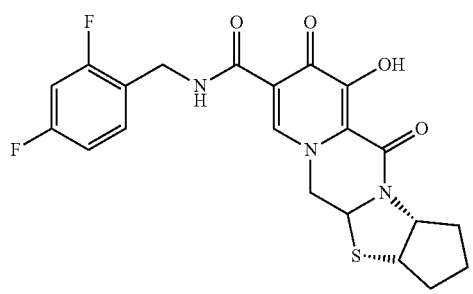
51
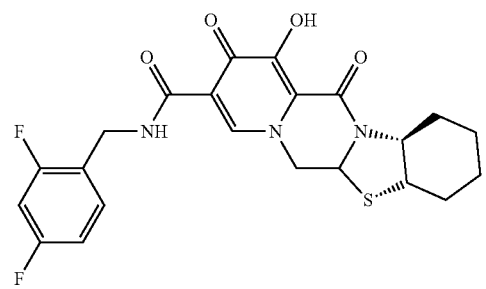
52
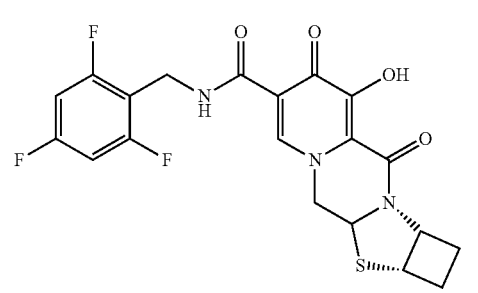
53
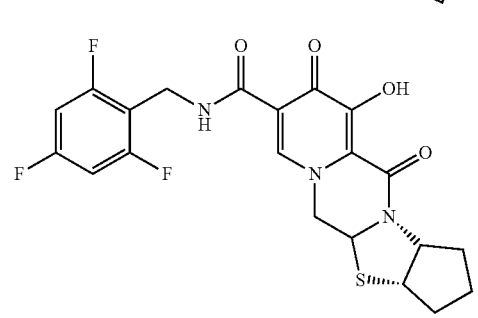
54
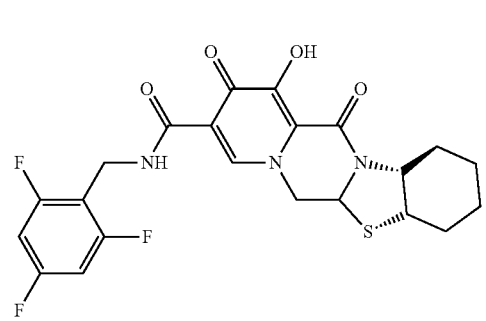
55
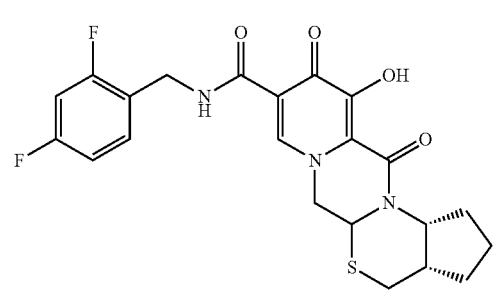

-continued
56
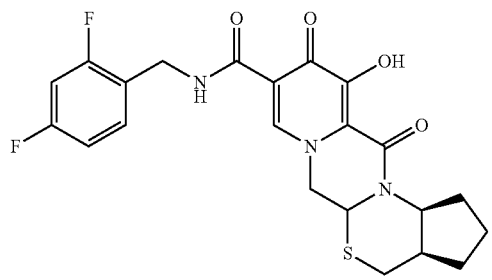
57
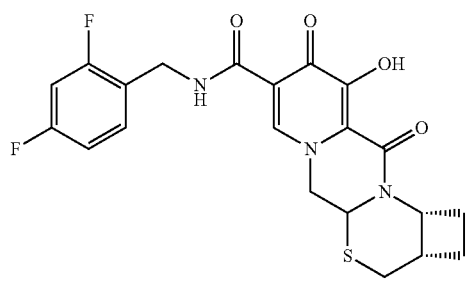
58
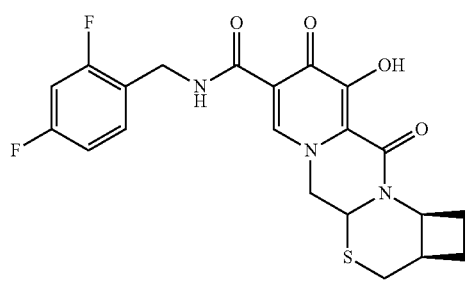
59
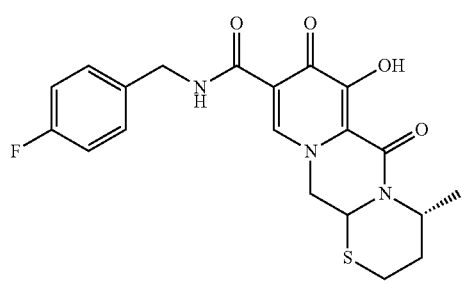
60
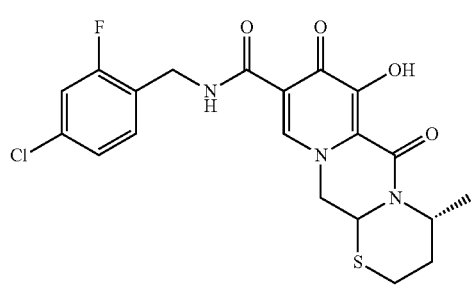
-continued
61
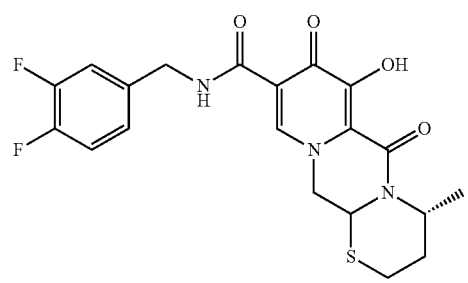
62
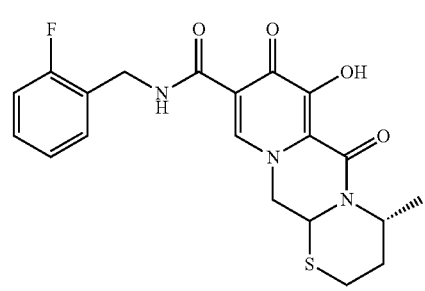
63
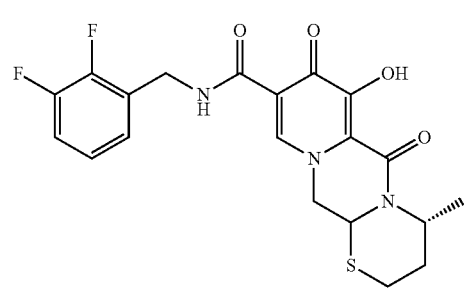
64
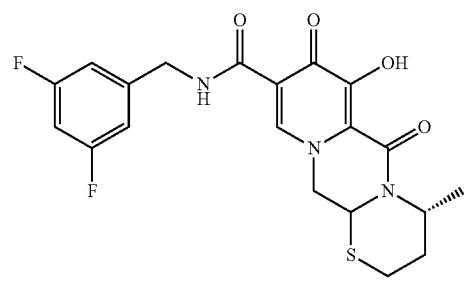
65
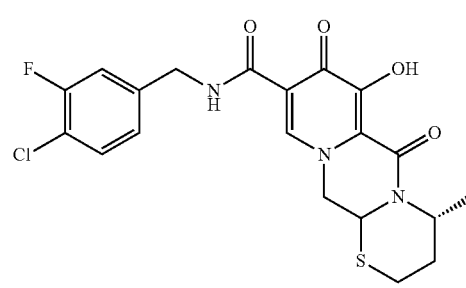

66
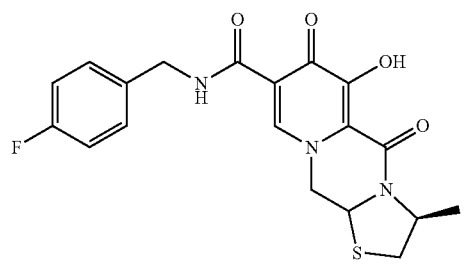
67
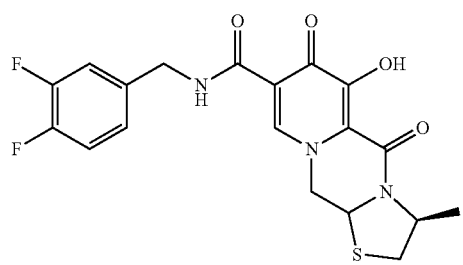
68
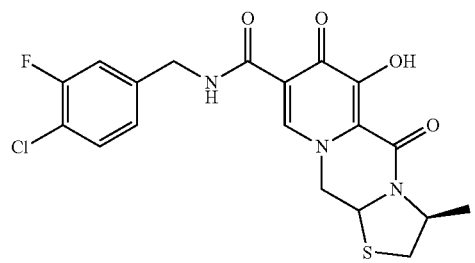
69
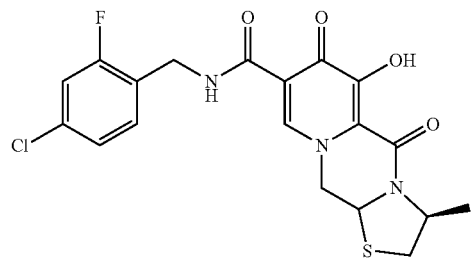
70
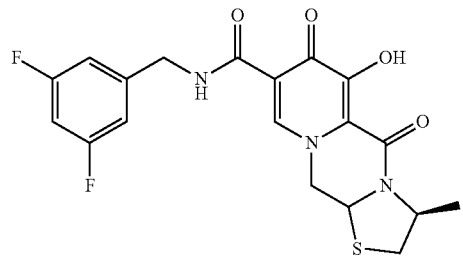
71
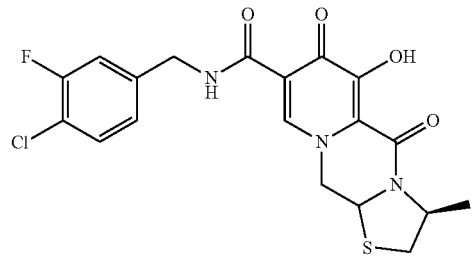
72
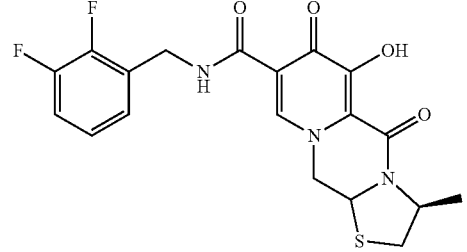
73
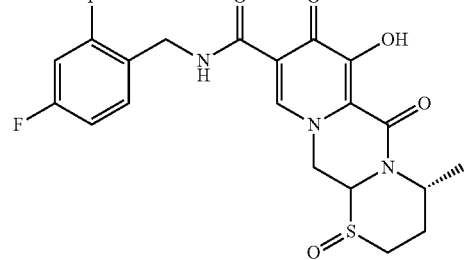
74
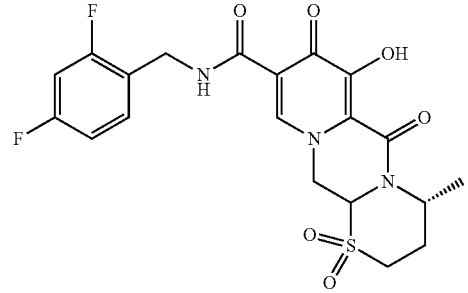
75
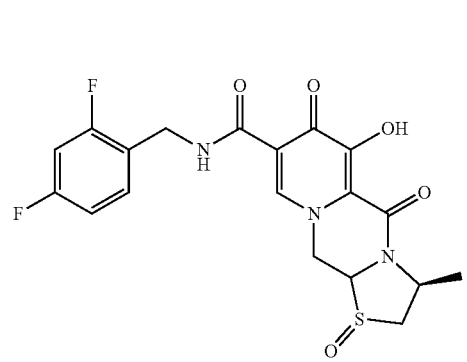
76
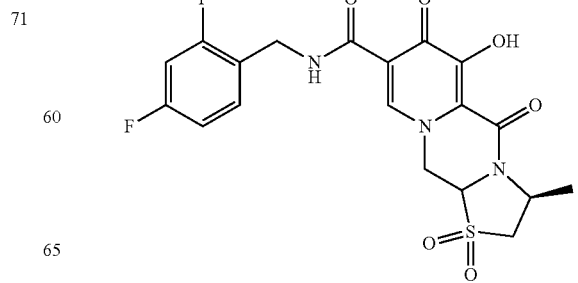

77
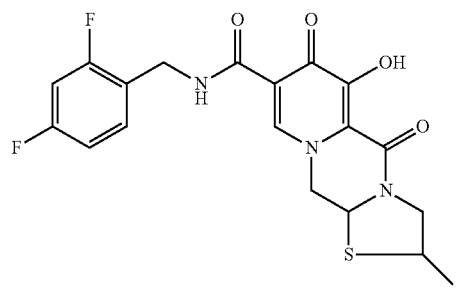
78
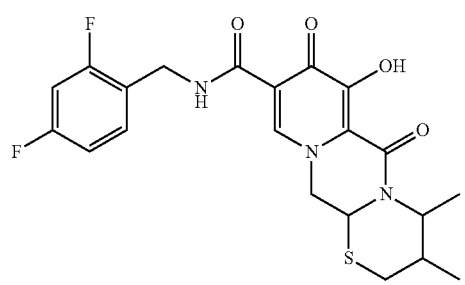
79
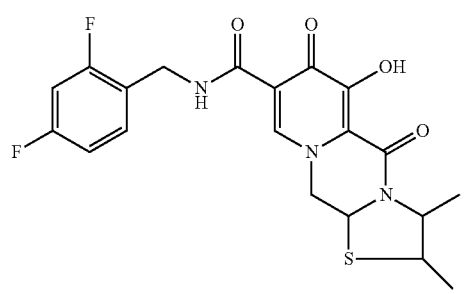
80
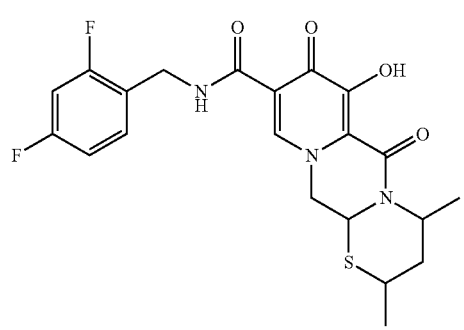
81
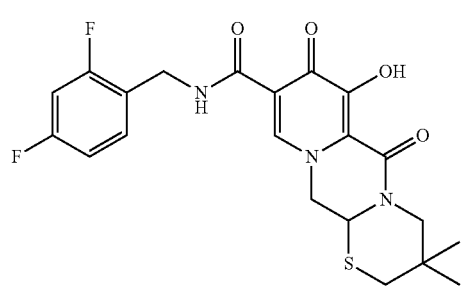
82
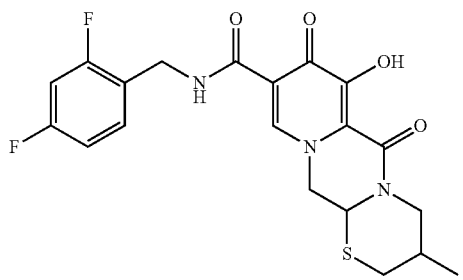
83
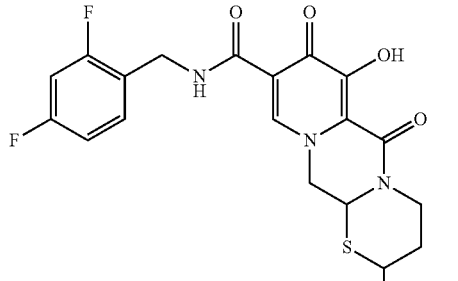
84
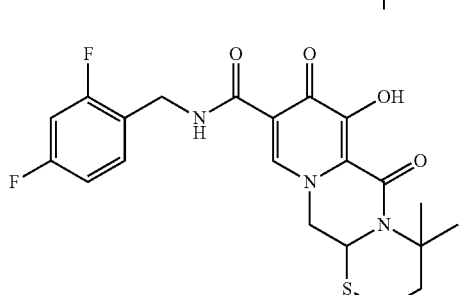
85
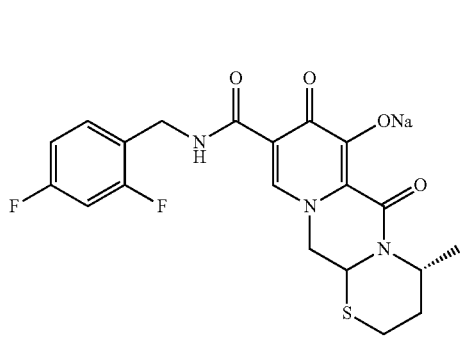
86
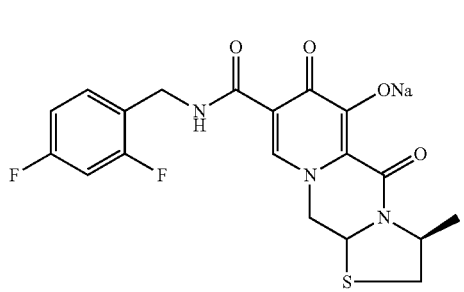

87

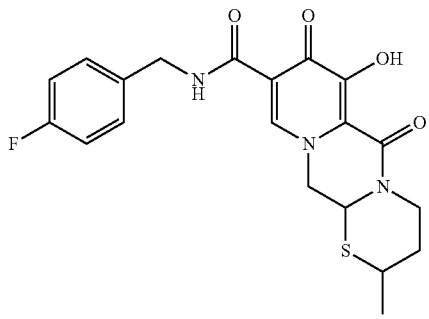

88

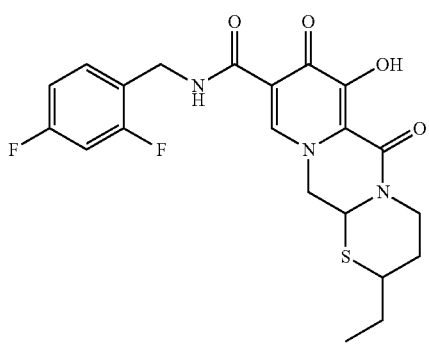

89

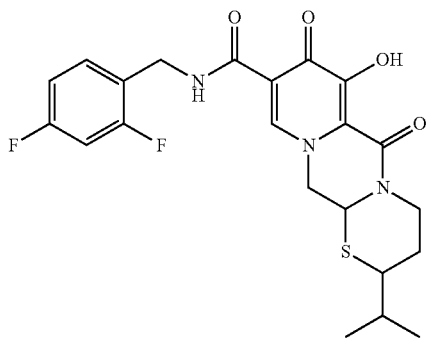

90

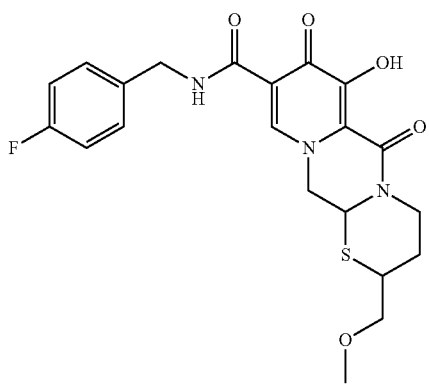

91

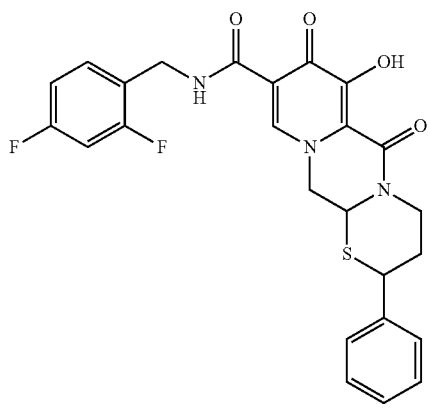

92

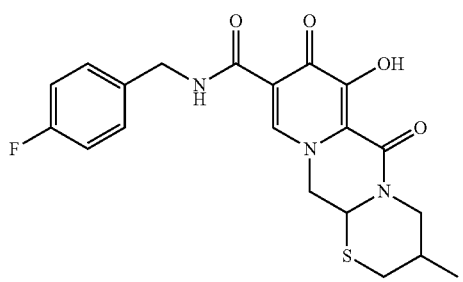

93

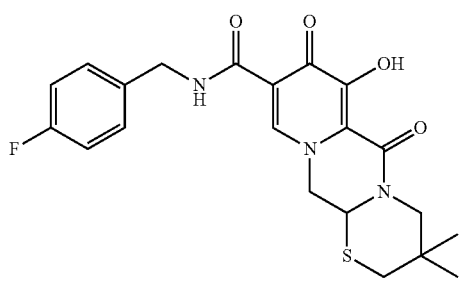

Preferably, the pharmaceutically acceptable salt is a sodium salt or a potassium salt.

The disclosure also provides a pharmaceutical composition, comprising the compound according to any one of claims 1~5 or a pharmaceutically acceptable salt thereof or a solvate thereof as an active ingredient.

Preferably, the pharmaceutical composition further comprises one or more additional anti-HIV therapeutic agents.

Preferably, the pharmaceutical composition further comprises a pharmaceutically acceptable carrier.

The disclosure also provides application of the compound or the pharmaceutically acceptable salt thereof or the solvate thereof in preparation of anti-HIV drugs. The anti-HIV drug is an anti-AIDS drug.

The disclosure also provides a method for preparing the compound A3, wherein the method is as follows:

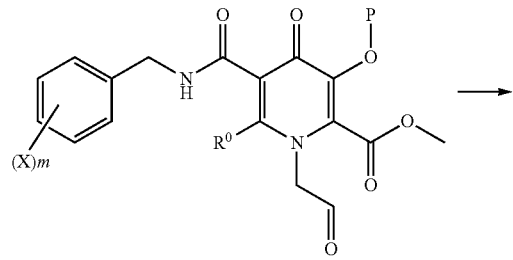

A1

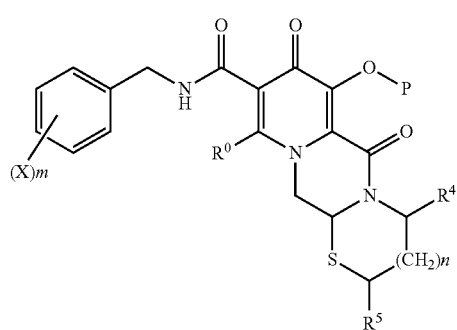

A2

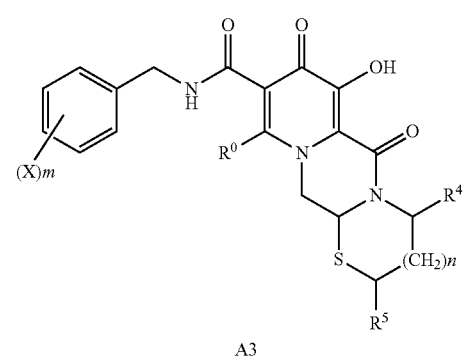

A3

The compound A1 and an aminothiol compound are heated and condensed under the catalysis of acid to be converted into compound A2, and the protection group P of the compound A2 is removed to generate the compound A3.

The disclosure also provides another method for preparing the compound A3, wherein the method is as follows:

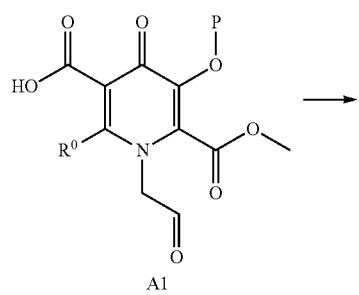

A1

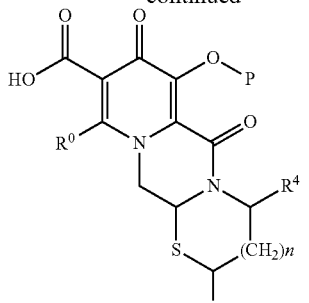

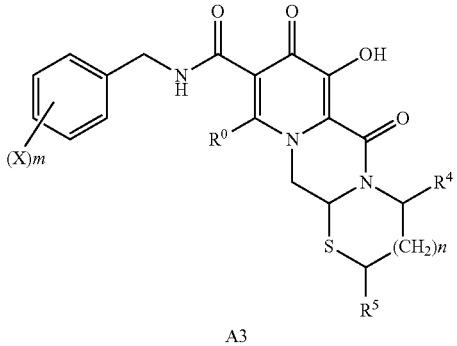

A2

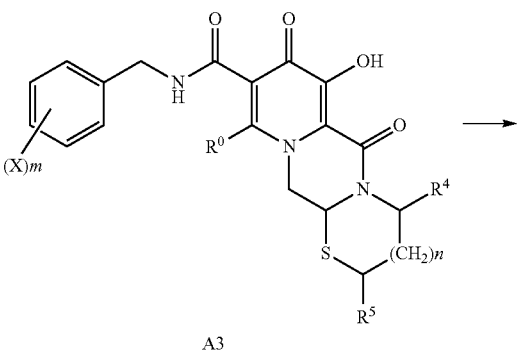

A3 the compound A4 and an aminothiol compound are heated and condensed under the catalysis of acid to generate compound A5; the compound A5 is converted into amide through amine and a coupling agent, and then the protection group P is removed to obtain the compound A3.

The disclosure also provides a method for preparing the compound A6, wherein the method is as follows:

A3

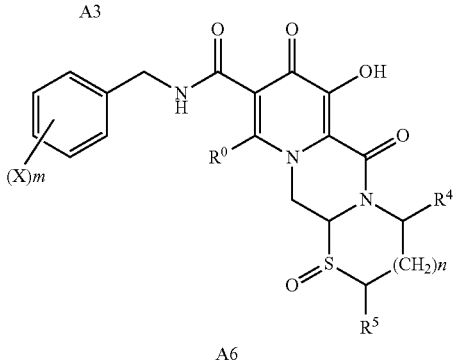

A6 the compound A3 is converted into the compound A6 by adding an oxidant such as peroxidized organic acids (m-CPBA or peracetic acid or per peroxidized trifuloroacetic acid or the like) or hydrogen peroxide (phosphomolybdic acid catalysis) or peroxidized tertiary butanol.

The disclosure also provides a method for preparing the compound A7, wherein the method is as follows:

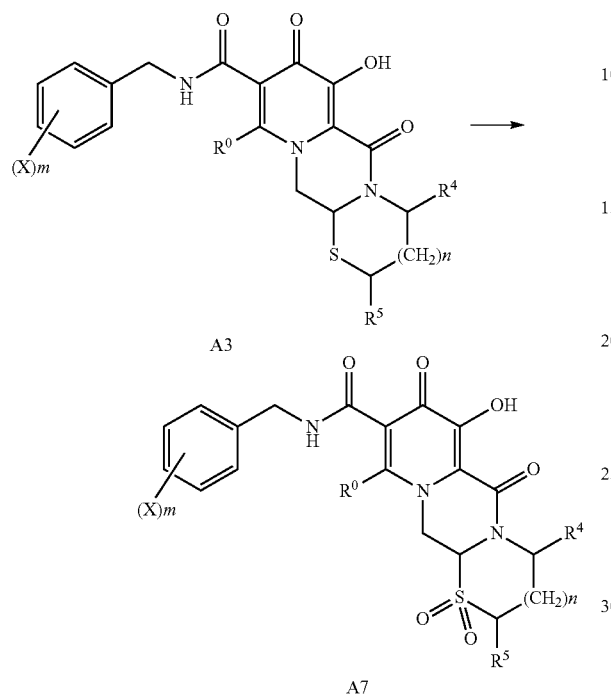

the compound A3 is converted into the compound A7 by adding an oxidant such as peroxidized organic acids (m-CPBA or peracetic acid or per peroxidized trifuloroacetic acid or the like) or hydrogen peroxide (phosphomolybdic acid catalysis) or peroxidized tertiary butanol.

Compared with the prior art, the disclosure has the beneficial effects:

The sulfur-containing polycyclic-hydroxypyridone carboxamide analogs provided by the disclosure all have good anti-HIV activity, and in particular, compound 2, compound 18, compound 34 and compound 66 have strong inhibitory effect on HIV-1 replication in vitro, and the therapeutic index of the analog against HIV is hundreds of times greater than that of the existing drugs TDF and Dolutegravir. The development of such the compounds is of great significance for the development of AIDS drugs and will bright good news to AIDS patients.

DETAILED DESCRIPTION OF PREFERRED EMBODIMENTS

Next, the technical solution of the disclosure will be described through embodiments. Raw materials and reagents used in the disclosure are all commercially available.

A general synthesis solution of a sulfur-containing polycyclic-hydroxypyridone carboxamide analog of the disclosure is as follows:

Solutions 1-3 are provided as further embodiments of the disclosure, and a general method for preparing a compound having formula (I) and preparing another compound having formula (I) is exemplified.

Solution 1

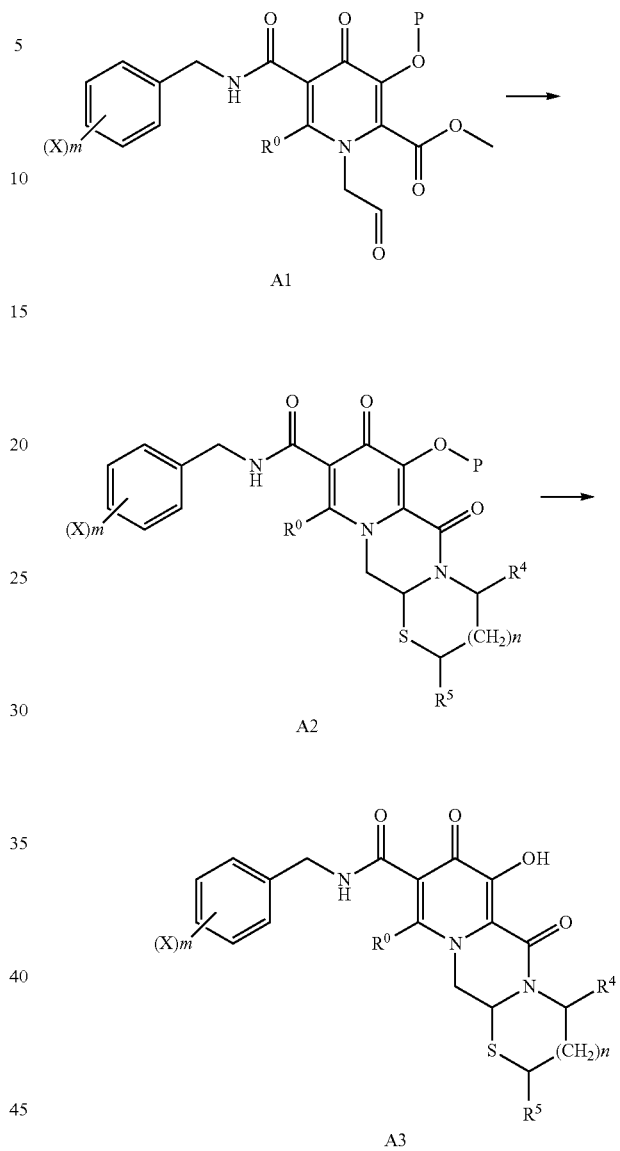

By heating and condensing A1 and proper amino mercaptan under the catalysis of proper acid, A1 can be converted into A2, and the protecting group P of A2 is subsequently removed to form A3.

Solution 2

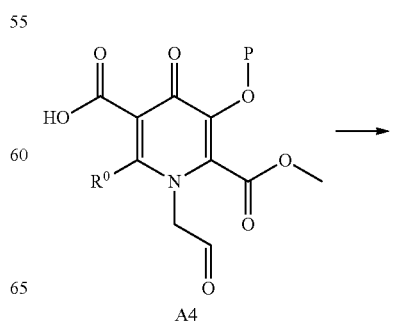

31
-continued

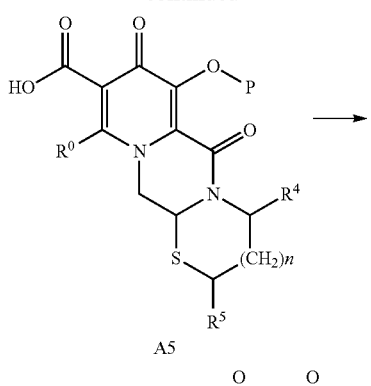
A5

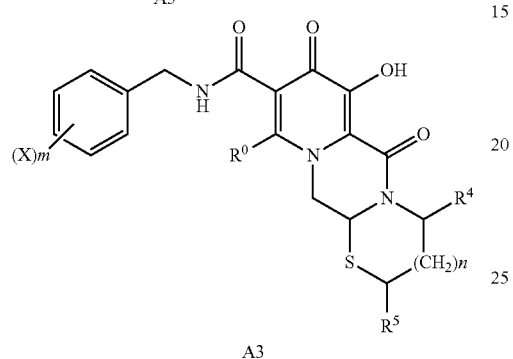
A3

By heating and condensing A4 and proper amino mercaptan under the catalysis of proper acid, A4 is converted into A5. By using proper amine and a coupling reagent such as HATU or CDI or HOBt, A5 is converted into amine, and subsequently, the protective group P of A5 is removed to form A3.

Solution 3

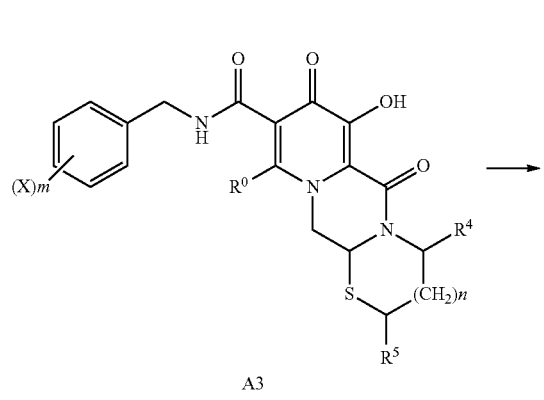
A3

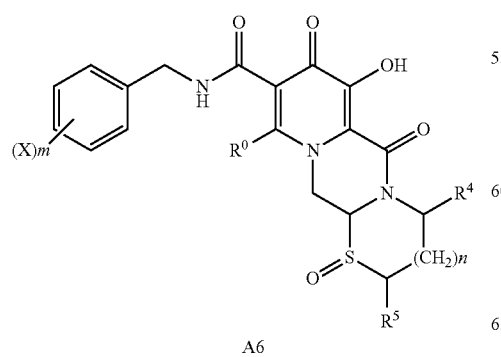
A6

32
-continued

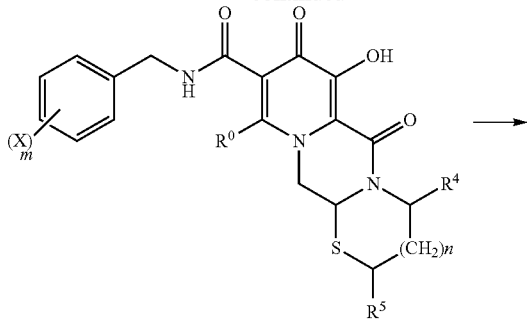
A3

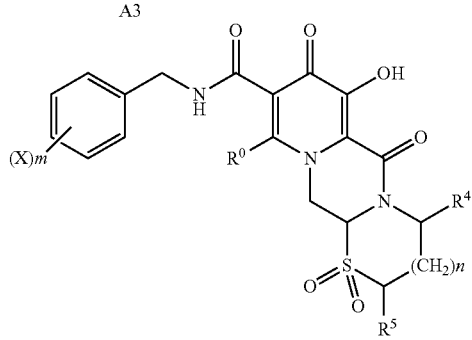
A7

By using a proper oxidant, A3 is converted into sulfoxide A6 or sulfone A7

Example 1

Preparation of Compound 1

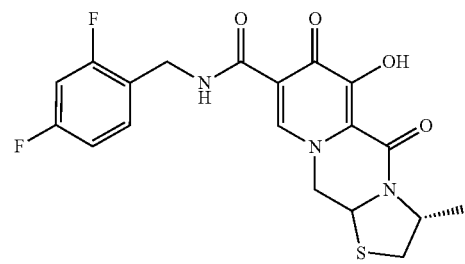
1

The preparation routine of the compound is as follows:

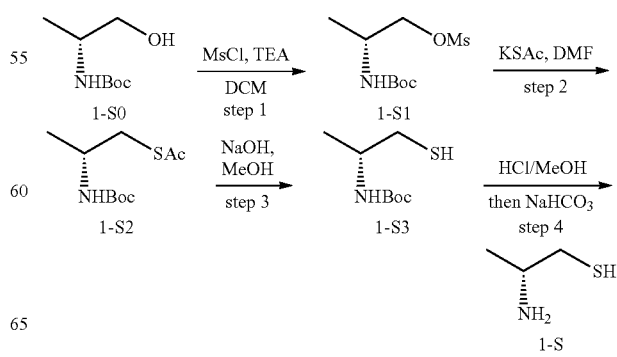

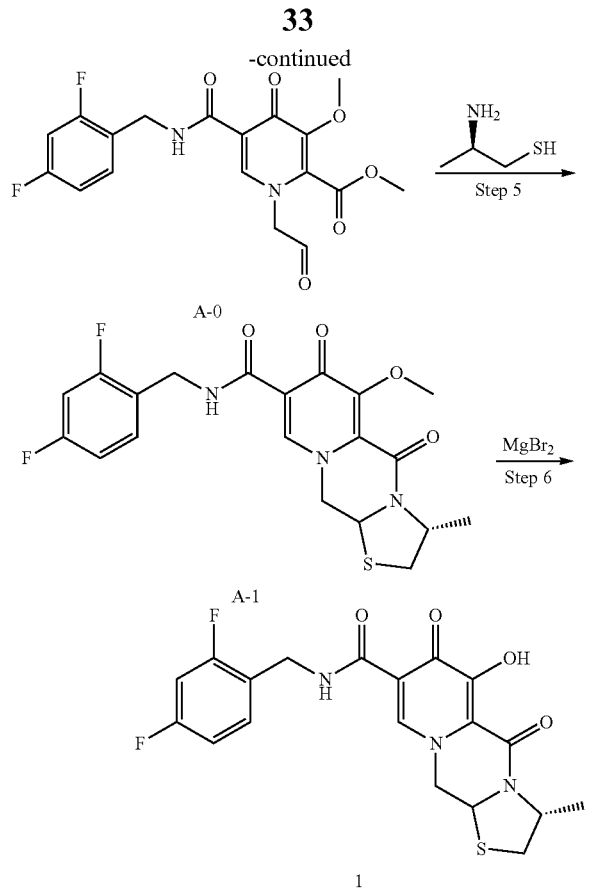

The specific steps of the compound are as follows:

Step 1

Methylsulfonyl chloride (1.3 g, 11 mmol) was dropwise added into the solution of compound 1-S0: (2R)-2-(Boc-amino)-1-propanol (1.75 g, 10 mmol) and triethylamine (2.1 g, 20 mmol) in DCM (30 mL) at 0° C. The reaction mixture was stirred at the same temperature for about 2 h, followed by quenching with water, the separated organic layer was respectively washed with in 1N diluted hydrochloric acid and brine, then dried with sodium sulfate and concentrated to give crude product 1-S1 (2.5 g); the crude product was directly used for next reaction without purification.

Step 2

Potassium thioacetate (1.7 g, 15 mmol) was dissolved into DMF (10 mL) and then the above mixture was added to the solution of the crude product intermediate 1-S1 (2.5 g, 10 mmol) from step 1 in DMF (15 mL). The reaction mixture was stirred at 60° C. for 3 h. The reaction was cooled to room temperature, diluted with methyl tert-butyl ether (80 mL) and was washed with brine, dried with sodium sulfate and concentrated to give crude product 1-S2 (2.5 g); the crude product was directly used for next reaction without purification.

Step 3

The crude product intermediate 1-S2 (2.5 g) from step 2 was dissolved into methanol (15 mL) and then sodium hydroxide (400 mg, 10 mmol) was added to the above mixture. The reaction mixture was stirred at room temperature for 2 h then methanol was removed by concentration, methyl tert-butyl ether was added, pH was adjusted to 3, and the separated organic layer was washed with brine, and dried with sodium sulfate and concentrated to obtain crude product 1-S3 (2.0 g); the crude product was directly used for next reaction without purification.

Step 4

The crude product intermediate 1-S3 (2.0 g) from step 3 was dissolved into 2N hydrogen chloride-methanol solution (20 mL). The reaction mixture was stirred at room temperature for 2 h then the hydrogen chloride-methanol solution was removed by concentration to give residue, methyl tert-butyl ether was added to the residue. After stirring for 2 h solid precipitated, then the filtrated solid, namely 1-S(2R)-2-amino-1-propanethiol hydrochloride (0.8 g), was dissolved into methanol, then sodium carbonate (840 mg) was added to neutralize hydrochloride, the obtained product was filtrated, and the filtrate was concentrated to obtain 1-S, namely, (2R)-2-amino-1-propanethiol (600 mg).

Step 5

(2R)-2-amino-1-propanethiol (136 mg, 1.5 mol) and acetate acid (60 mg) were added to the solution of A-0 (395 mg, 1 mmol) in dichloroethane (40 mL). Then the reaction mixture was refluxed for 2 h. After cooling, the reaction mixture was concentrated under reduced pressure to provide a residue, which was purified by silica column chromatography (elution with a gradient of 0-5% methyl alcohol/dichloromethane) to provide compound A-1 (310 mg, 70% yield). $^1$H-NMR (400 MHz, CDCl$_3$) 10.41 (br, 1H), 8.41 (s, 1H), 7.36 (m, 1H), 6.82 (m, 2H), 5.24-5.10 (m, 2H), 4.64 (m, 2H), 4.28 (m, 1H), 4.12 (m, 1H), 4.08 (s, 3H), 3.31 (m, 1H), 2.82 (m, 1H), 1.45 (d, J=6.4 Hz, 3H). ESI$^+$ (m/z): 436 (M+1).

Step 6

Magnesium bromide (200 mg, 1.68 mmol) was added to the solution of A-1 (220 mg, 0.5 mmol) in acetonitrile (10 ml) at room temperature before the resulting mixture was stirred at 50° C. for 2 h. After the reaction mixture was stirred at 0° C., 0.5N diluted hydrochloric acid (10 mL) was added to make the mixture a solution. The resulting solution was diluted with water (50 mL) and extracted with dichloromethane (50 mL), the extract was dried with anhydrous magnesium sulfate and concentrated. The residue was purified by silica column chromatography (elution with a gradient of 0-5% methyl alcohol/dichloromethane) to provide Compound 1 (162 mg, 75% yield) $^1$H-NMR (400 MHz, CDCl$_3$) δ 12.00 (br, 1H), 10.40 (br, 1H), 8.42 (s, 1H), 7.38 (m, 1H), 6.83 (m, 2H), 5.23-5.12 (m, 2H), 4.73-4.45 (m, 2H), 4.24 (m, 1H), 4.10 (m, 1H), 3.35 (m, 1H), 2.90 (m, 1H), 1.46 (d, J=6.4 Hz, 3H). ESI$^+$ (m/z): 422 (M+1).

Example 2

Preparation of Compound 2

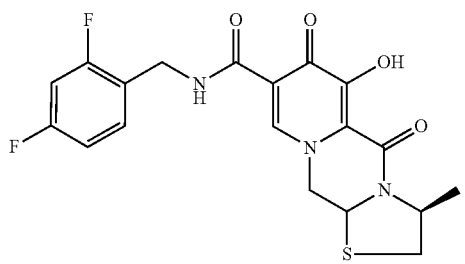

Compound 2 was prepared by using the method of compound 1 and replacing (2R)-2-(Boc-amino)-1-propanol with (S)-2-(Boc-amino)-1-propanol. $^1$H-NMR (400 MHz, CDCl$_3$) δ 11.84 (br, 1H), 10.39 (br, 1H), 8.41 (s, 1H), 7.39 (m, 1H), 6.84 (m, 2H), 5.21-5.11 (m, 2H), 4.75-4.47 (m, 2H), 4.23 (m, 1H), 4.10 (m, 1H), 3.35 (m, 1H), 2.87 (m, 1H), 1.48 (d, J=6.8 Hz, 3H). ESI⁺ (m/z): 422 (M+1).

Example 3

Preparation of Compound 3

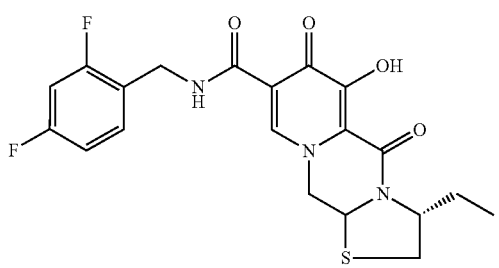

3

Compound 3 was prepared by using the method of compound 1 and replacing (2R)-2-(Boc-amino)-1-propanol-1-propanol with (2R)-2-(Boc-amino)-1-butanol. ¹H-NMR (400 MHz, CDCl₃) δ 10.40 (br, 1H), 8.38 (s, 1H), 7.33 (m, 1H), 6.80 (m, 2H), 5.21 (m, 2H), 4.60 (m, 2H), 4.22 (m, 1H), 4.08 (m, 1H), 3.32 (m, 1H), 2.90 (m, 1H), 2.11 (m, 1H), 1.72 (m, 1H), 0.97 (m, 3H). ESI⁺ (m/z): 436 (M+1).

Example 4

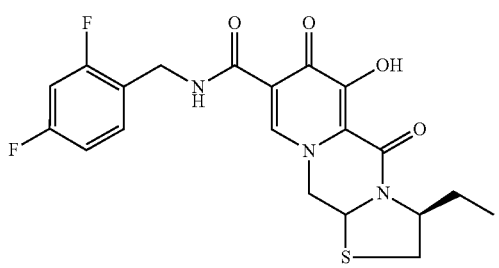

4

Compound 4 was prepared by using the method of compound 1 and replacing (2R)-2-(Boc-amino)-1-propanol-1-propanol with (2 S)-2-(Boc-amino)-1-butanol. ¹H-NMR (400 MHz, CDCl₃) δ 11.88 (br, 1H), 10.41 (br, 1H), 8.39 (s, 1H), 7.35 (m, 1H), 6.81 (m, 2H), 5.20 (m, 2H), 4.61 (m, 2H), 4.20 (m, 1H), 4.09 (m, 1H), 3.33 (m, 1H), 2.90 (m, 1H), 2.10 (m, 1H), 1.71 (m, 1H), 0.96 (m, 3H). ESI⁺ (m/z): 436 (M+1).

Example 5

Preparation of Compound 5

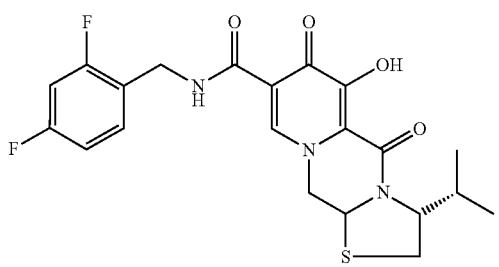

5

Compound 5 was prepared by using the method of compound 1 and replacing (2R)-2-(Boc-amino)-1-propanol with (2R)-2-(Boc-amino)-3-methyl-1-butanol. ¹H-NMR (400 MHz, CDCl₃) δ 11.93 (br, 1H), 10.30 (br, 1H), 8.43 (s, 1H), 7.36 (m, 1H), 6.82 (m, 2H), 5.23 (m, 2H), 4.63 (m, 2H), 4.22 (m, 1H), 4.12 (m, 1H), 3.33 (m, 1H), 2.92 (m, 1H), 2.32 (m, 1H), 0.99 (m, 6H). ESI⁺ (m/z): 450 (M+1).

Example 6

Preparation of Compound 6

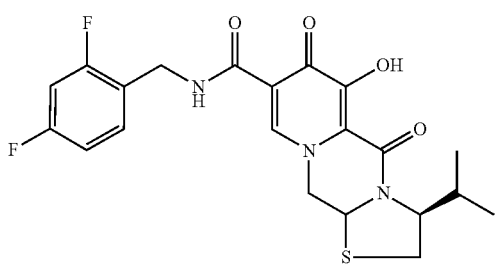

6

Compound 6 was prepared by using the method of compound 1 and replacing (2R)-2-(Boc-amino)-1-propanol with (2S)-2-(Boc-amino)-3-methyl-1-butanol. ¹H-NMR (400 MHz, CDCl₃) δ 11.91 (br, 1H), 10.39 (br, 1H), 8.40 (s, 1H), 7.35 (m, 1H), 6.80 (m, 2H), 5.22 (m, 2H), 4.61 (m, 2H), 4.21 (m, 1H), 4.11 (m, 1H), 3.32 (m, 1H), 2.91 (m, 1H), 2.33 (m, 1H), 0.98 (m, 6H). ESI⁺ (m/z): 450 (M+1).

Example 7

Preparation Method of Compound 7

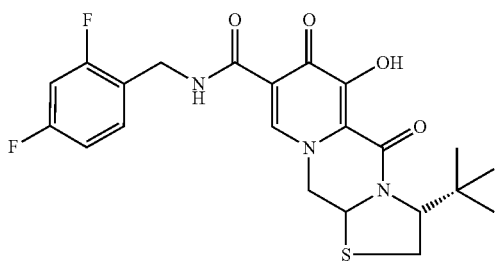

7

Compound 7 was prepared by using the method of compound 1 and replacing (2R)-2-(Boc-amino)-1-propanol with (2R)-2-(Boc-amino)-3,3-dimethyl-1-butanol. ¹H-NMR (400 MHz, CDCl₃) δ 10.35 (br, 1H), 8.38 (s, 1H), 7.34 (m, 1H), 6.79 (m, 2H), 5.25 (m, 2H), 4.61 (m, 2H), 4.23 (m, 1H), 4.13 (m, 1H), 3.33 (m, 1H), 2.90 (m, 1H), 1.05 (m, 9H). ESI⁺ (m/z): 464 (M+1).

Example 8

Preparation of Compound 8

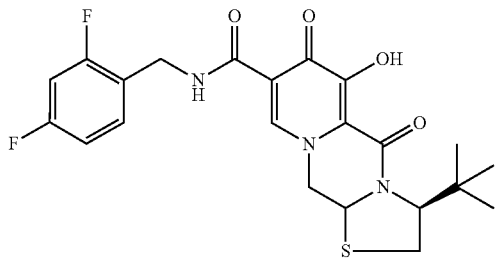

8

Compound 8 was prepared by using the method of compound 1 and replacing (2R)-2-(Boc-amino)-1-propanol with (2S)-2-(Boc-amino)-3,3-dimethyl-1-butanol. $^1$H-NMR (400 MHz, CDCl$_3$) δ 10.38 (br, 1H), 8.41 (s, 1H), 7.34 (m, 1H), 6.81 (m, 2H), 5.27 (m, 2H), 4.62 (m, 2H), 4.22 (m, 1H), 4.13 (m, 1H), 3.32 (m, 1H), 2.91 (m, 1H), 1.01 (m, 9H). ESI$^+$ (m/z): 464 (M+1).

Example 9

Preparation of Compound 9

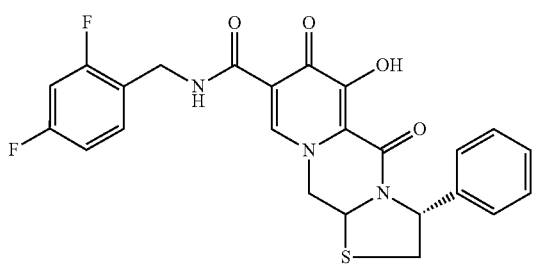

9

Compound 9 was prepared by using the method of compound 1 and replacing (2R)-2-(Boc-amino)-1-propanol with (2R)-2-(Boc-amino)-2-benzyl-1-ethanol. $^1$H-NMR (400 MHz, CDCl$_3$) δ 11.86 (br, 1H), 10.40 (br, 1H), 8.40 (s, 1H), 7.45-7.30 (m, 6H), 6.81 (m, 2H), 5.60 (m, 1H), 5.25 (m, 1H), 4.75-4.47 (m, 2H), 4.25 (m, 1H), 4.13 (br, 1H), 3.33 (m, 1H), 2.90 (m, 1H). ESI$^+$ (m/z): 484 (M+1).

Example 10

Preparation of Compound 10

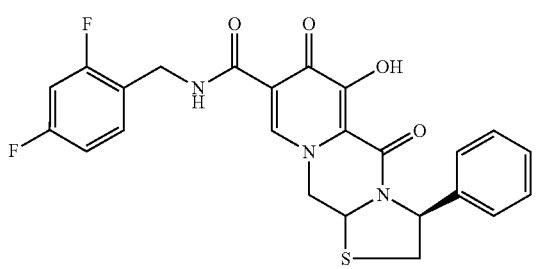

10

Compound 10 was prepared by using the method of compound 1 and replacing (2R)-2-(Boc-amino)-1-propanol with (2R)-2-(Boc-amino)-2-benzyl-1-ethanol. $^1$H-NMR (400 MHz, CDCl$_3$) δ 11.86 (br, 1H), 10.40 (br, 1H), 8.40 (s, 1H), 7.45-7.30 (m, 6H), 6.81 (m, 2H), 5.60 (m, 1H), 5.25 (m, 1H), 4.75-4.47 (m, 2H), 4.25 (m, 1H), 4.13 (br, 1H), 3.33 (m, 1H), 2.90 (m, 1H). ESI$^+$ (m/z): 484 (M+1).

Example 11

Preparation of Compound 12

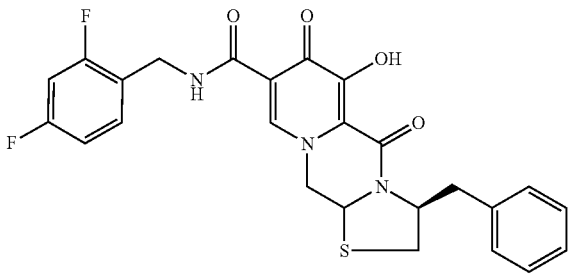

12

Compound 12 was prepared by using the method of compound 1 and replacing (2R)-2-(Boc-amino)-1-propanol with (2 S)-2-(Boc-amino)-3-benzyl-1-propanol. $^1$H-NMR (400 MHz, CDCl$_3$) δ 11.88 (br, 1H), 10.40 (br, 1H), 8.40 (s, 1H), 7.39-7.15 (m, 6H), 6.83 (m, 2H), 5.20-5.08 (m, 2H), 4.75-4.47 (m, 2H), 4.25 (m, 1H), 4.13 (m, 1H), 3.36-3.33 (m, 2H), 2.96-2.88 (m, 2H). ESI$^+$ (m/z): 498 (M+1).

Example 12

Preparation of Compound 19

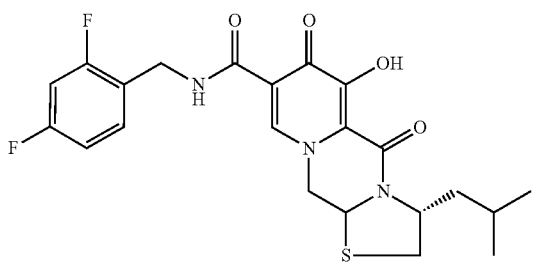

19

Compound 19 was prepared by using the method of compound 1 and replacing (2R)-2-(Boc-amino)-1-propanol with (2R)-2-(Boc-amino)-4-methyl-1-pentanol. $^1$H-NMR (400 MHz, CDCl$_3$) δ 12.01 (br, 1H), 10.40 (br, 1H), 8.41 (s, 1H), 7.39 (m, 1H), 6.82 (m, 2H), 5.24-5.12 (m, 2H), 4.74-4.43 (m, 2H), 4.25 (m, 1H), 4.11 (m, 1H), 3.35 (m, 1H), 2.91 (m, 1H), 2.06 (m, 1H), 1.65 (m. 1H), 1.41 (m, 1H), 0.99 (m, 6H). ESI$^+$ (m/z): 464 (M+1).

Example 13

Preparation of Compound 20

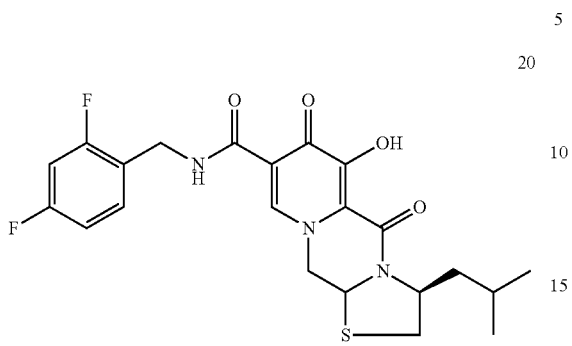

Compound 20 was prepared by using the method of compound 1 and replacing (2R)-2-(Boc-amino)-1-propanol with (2S)-2-(Boc-amino)-4-methyl-1-pentanol. ¹H-NMR (400 MHz, CDCl₃) δ 12.00 (br, 1H), 10.41 (br, 1H), 8.40 (s, 1H), 7.37 (m, 1H), 6.80 (m, 2H), 5.23-5.12 (m, 2H), 4.74-4.43 (m, 2H), 4.23 (m, 1H), 4.10 (m, 1H), 3.34 (m, 1H), 2.90 (m, 1H), 2.04 (m, 1H), 1.63 (m, 1H), 1.40 (m, 1H), 1.0 (m, 6H). ESI⁺ (m/z): 464 (M+1).

Example 14

Preparation of Compound 17

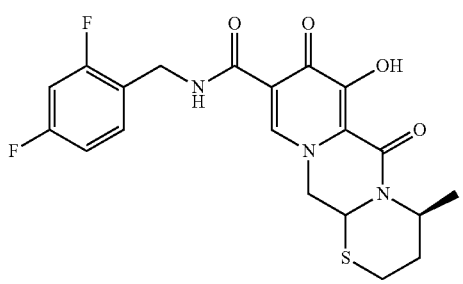

Compound 17 was prepared by using the method of compound 1 and replacing (2R)-2-(Boc-amino)-1-propanol with (3S)-3-(Boc-amino)-1-butanol. ¹H-NMR (400 MHz, CDCl₃) δ 12.46 (s, 1H), 10.42 (br, 1H), 8.31 (s, 1H), 7.35 (m, 1H), 6.82 (m, 2H), 5.23-5.12 (m, 2H), 4.66-4.45 (m, 2H), 4.12 (d, J=13.6 Hz, 1H), 3.30 (m, 1H), 2.70 (m, 1H), 2.09 (m, 1H), 1.81 (m. 1H), 1.40 (d, J=6.8 Hz, 3H). ESI⁺ (m/z): 436 (M+1).

Example 15

Preparation of Compound 18

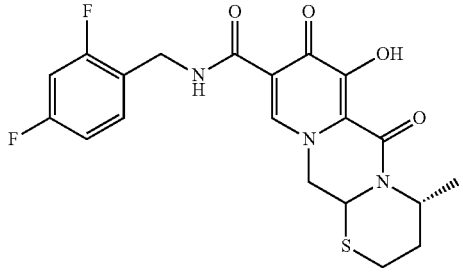

Compound 18 was prepared by using the method of compound 1 and replacing (2R)-2-(Boc-amino)-1-propanol with (3R)-3-(Boc-amino)-1-butanol. ¹H-NMR (400 MHz, CDCl₃) δ 12.45 (s, 1H), 10.42 (br, 1H), 8.32 (s, 1H), 7.36 (m, 1H), 6.82 (m, 2H), 5.23-5.12 (m, 2H), 4.65-4.47 (m, 3H), 4.11 (d, J=13.6 Hz, 1H), 3.31 (m, 1H), 2.71 (m, 1H), 2.10 (m, 1H), 1.83 (m, 1H), 1.38 (d, J=6.8 Hz, 3H). ESI⁺ (m/z): 436 (M+1).

Example 16

Preparation of Compound 26

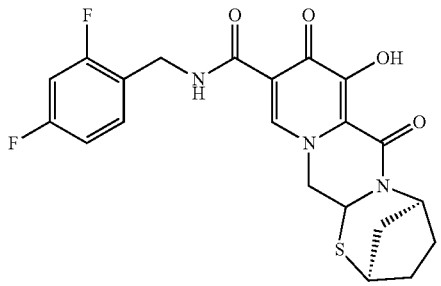

Compound 26 was prepared by using the method of compound 1 and replacing (2R)-2-(Boc-amino)-1-propanol with (1S,3S)-3-(Boc-amino)-1-cyclopentanol. ¹H-NMR (400 MHz, CDCl₃) δ 12.46 (s, 1H), 10.45 (br, 1H), 8.33 (s, 1H), 7.36 (m, 1H), 6.85 (m, 2H), 5.33 (m, 1H), 4.72 (m, 2H), 4.09 (m, 1H), 3.95-3.72 (m, 2H), 3.35 (m, 1H), 1.96 (s, 4H), 1.81 (d, J=12 Hz, 1H), 1.62 (t, J=12.4 Hz, 1H). ESI⁺ (m/z): 448 (M+1).

Example 17

Preparation of Compound 34

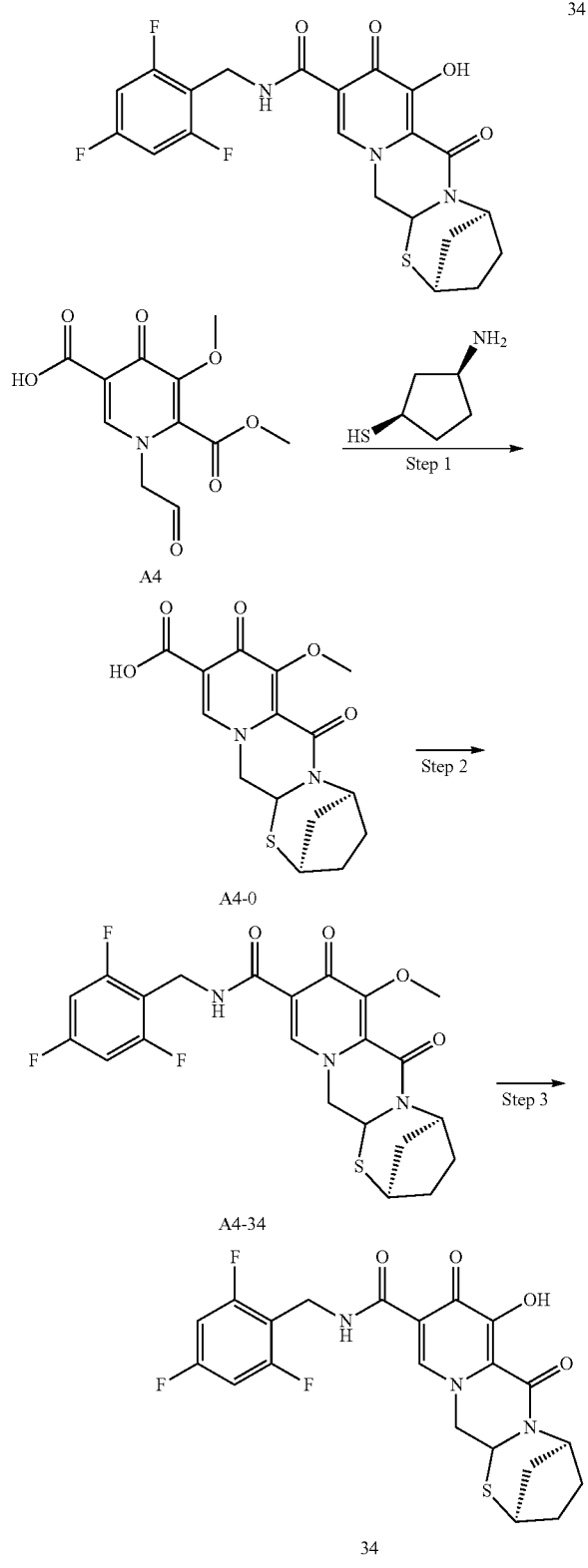

Step 1

(1R,3S)-3-amino-1-cyclopenthiol (176 mg, 1.5 mmol) and acetic acid (60 mg) were added the solution of compound A4 (269 mg, 1 mmol) in dichloroethane (50 mL). Then the reaction mixture was refluxed for 5 h. After cooling, dichloromethane was added, the diluted product was respectively washed with 0.5N HCl (5 mL) and brine, the extract was dried with anhydrous magnesium sulfate and concentrated to obtain crude product A4-0 (270 mg), and the crude product was directly used for next reaction without purification. LCMS-ESI⁻ (m/z): 335 (M−1).

Step 2

The crude product intermediate A4-0 (270 mg, 0.8 mmol) from step 1, 2-(7-azobenzotriazole)-N,N,N',N'-tetramethyl-urea hexafluorophosphate (HATU, 380 mg, 1 mmol) and 2,4,6-trifluorobenzylamine (161 mg, 1 mmol) were suspended in tetrahydrofuran (5 mL), and N,N-diisopropylethylamine (DIEPA, 200 mg, 1.6 mmol) was dropwise added at 0° C.; after dropwise addition, the temperature was raised to 25° C., the reaction was performed for 2 h, then dichloromethane (50 mL) was added for dilution, the diluted product was respectively washed with 0.5N diluted hydrochloric acid and brine, the extract was dried with anhydrous magnesium sulfate and concentrated to obtain the crude product A4-34 (350 mg). The crude product was directly used for next reaction without purification. LCMS-ESI⁻ (m/z): 480 (M+1).

Step 3

Magnesium bromide (200 mg, 1.68 mmol) was added the solution of the crude product intermediate A4-34 (350 mg, 0.7 mmol) from step 2 into acetonitrile (10 mL) at room temperature before the resulting mixture was stirred at 50° C. for 2 h. After the reaction mixture was stirred at 0° C., 0.5N diluted hydrochloric acid (10 mL) was added to make the mixture a solution. The resulting solution was diluted with water (50 mL) and extracted with dichloromethane (50 mL), the extract was dried with anhydrous magnesium sulfate and concentrated. The residue was purified by silica column chromatography (elution with a gradient of 0-5% methyl alcohol/dichloromethane) to provide the compound 34 (162 mg, 75% yield) ¹H-NMR (400 MHz, CDCl₃) δ 12.44 (s, 1H), 10.41 (br, 1H), 8.35 (s, 1H), 7.20 (m, 2H), 5.35 (m, 1H), 4.72 (m, 2H), 4.08 (m, 1H), 3.98-3.71 (m, 2H), 3.33 (m, 1H), 1.98 (s, 4H), 1.85 (d, J=12 Hz, 1H), 1.61 (t, J=12.4 Hz, 1H). ESI⁺ (m/z): 466 (M+1).

Example 18

Preparation of Compound 40

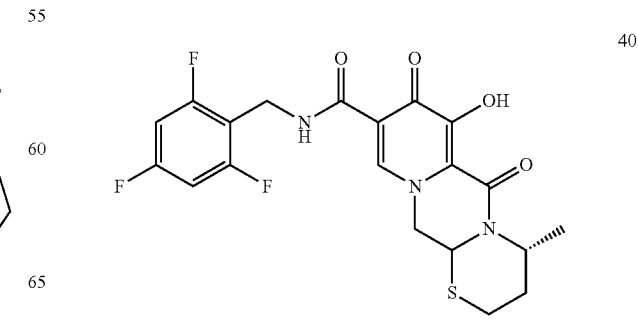

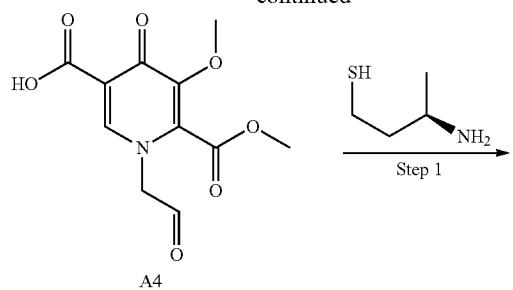

A4

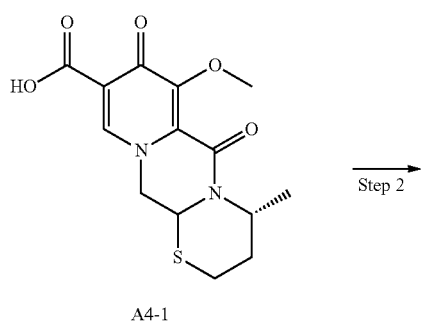

A4-1

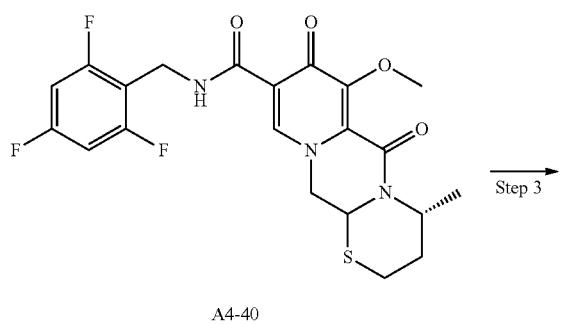

A4-40

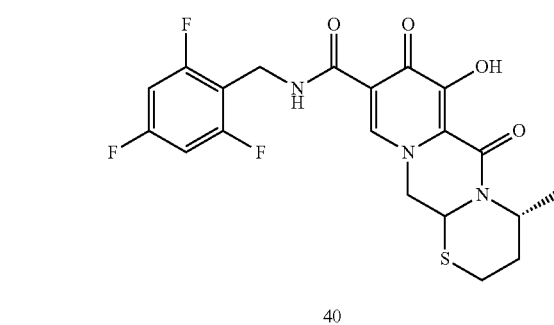

40

Step 1

(3R)-3-amino-1-butanethiol (160 mg, 1.5 mmol) and acetic acid (60 mg) were added added the solution of compound A4 (269 mg, 1 mmol) in dichloroethane (50 mL). Then the reaction mixture was refluxed for 2 h. After cooling, dichloromethane was added for dilution, the diluted product was respectively washed with 0.5N HCl (5 mL) and brine, the extract was dried with anhydrous magnesium sulfate and concentrated to obtain crude product A4-1 (260 mg), and the crude product was directly used for next reaction without purification. LCMS-ESI⁻ (m/z): 323 (M−1).

Step 2

The crude product intermediate A4-1 (260 mg, 0.8 mmol) from step 1, 2,-(7-azobenzotriazole)-N,N,N',N'-tetramethylurea hexafluorophosphate (HATU, 380 mg, 1 mmol) and 2,4,6-triflurobenzylamine (161 mg, 1 mmol) were suspended in tetrahydrofuran (5 mL), and then N,N-diisopropylethylamine (DIEPA, 200 mg, 1.6 mmol) was dropwise added at 0° C.; after dropwise addition, the temperature was raised to 25° C., the reaction was performed for 2 h, then dichloromethane (50 mL) was added for dilution, the diluted product was respectively washed with 0.5N diluted hydrochloric acid and saturated saline solution, the extract was dried with anhydrous magnesium sulfate and concentrated to obtain the crude product A4-40 (300 mg). The crude product was directly used for next reaction without purification. LCMS-ESI⁻ (m/z): 418 (M+1).

Step 3

Magnesium bromide (200 mg, 1.68 mmol) was added into the solution of the crude product intermediate A4-40 (300 mg, 0.64 mmol) in acetonitrile (10 mL) at room temperature before the resulting mixture was stirred at 50° C. for 2 h. After the reaction mixture was stirred at 0° C., 0.5N diluted hydrochloric acid (10 mL) was added to make the mixture a solution. The resulting solution was diluted with water (50 mL) and extracted with dichloromethane (50 mL), the extract was dried with anhydrous magnesium sulfate and concentrated. The residue was purified by silica column chromatography (elution with a gradient of 0-5% methyl alcohol/dichloromethane) to provide the compound 40 (150 mg, 51% yield). $^1$H-NMR (400 MHz, CDCl$_3$) δ 12.44 (s, 1H), 10.40 (br, 1H), 8.30 (s, 1H), 7.19 (m, 2H), 5.21-5.10 (m, 2H), 4.66-4.45 (m, 3H), 4.10 (m, 1H), 3.33 (m, 1H), 2.72 (m, 1H), 2.09 (m, 1H), 1.81 (m, 1H), 1.38 (d, J=7.2 Hz, 3H). ESI (m/z): 454 (M+1).

Example 19

Preparation of Compound 59

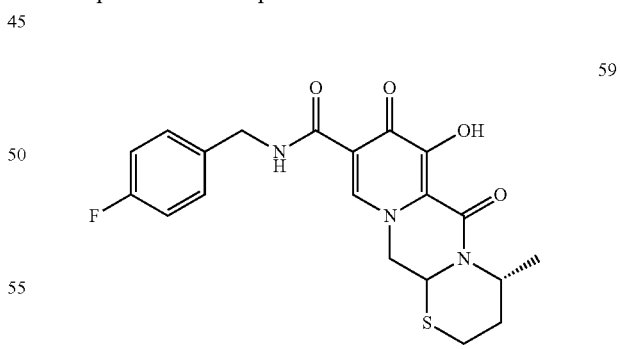

59

The compound 59 was prepared by using the preparation method of compound 40 and replacing 2,4,6-trifluorobenzylamine with p-fluorobenzylamine. $^1$H-NMR (400 MHz, CDCl$_3$) δ 12.40 (s, 1H), 10.40 (br, 1H), 8.33 (s, 1H), 7.30 (m, 2H), 7.00 (m, 2H), 5.23-5.12 (m, 2H), 4.62-4.40 (m, 3H), 4.10 (d, J=13.6 Hz, 1H), 3.30 (m, 1H), 2.70 (s, 1H), 2.8 (m, 1H), 1.80 (m, 1H), 1.36 (d, J=6.8 Hz, 3H). ESI⁺ (m/z): 418 (M+1).

Example 20

Preparation of Compound 66

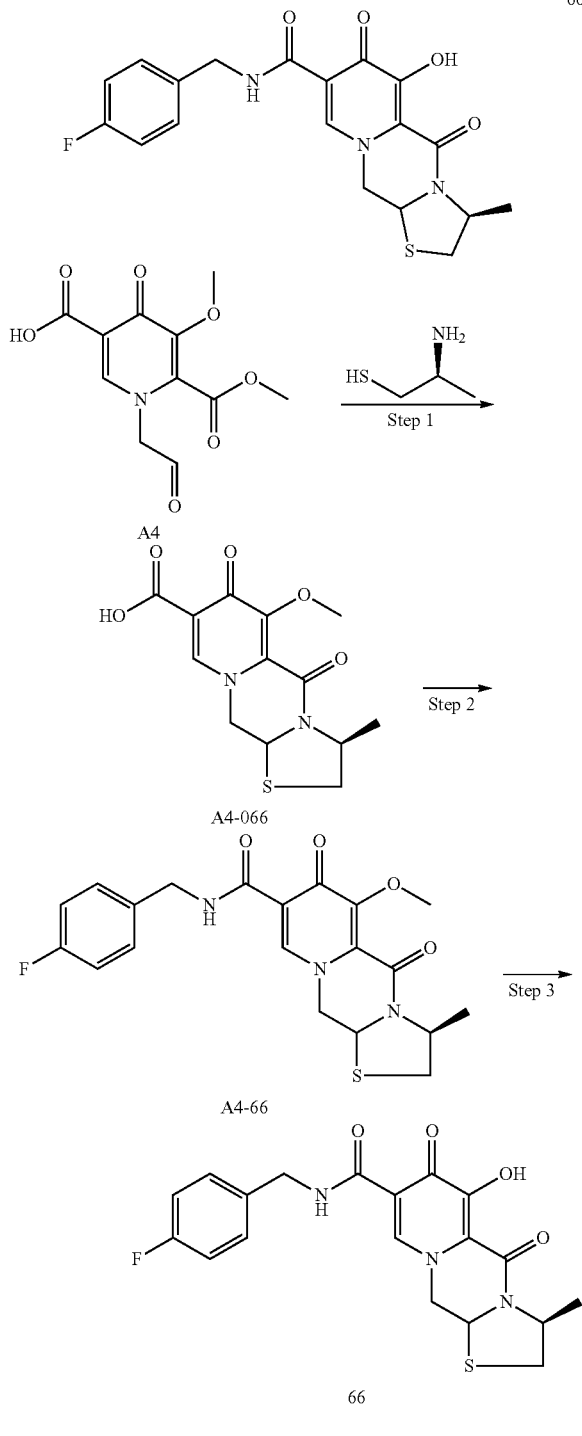

Step 1

(3S)-2-amino-1-propanethiol (155 mg, 1.5 mmol) and acetic acid (60 mg) were added into the solution of compound A4 (269 mg, 1 mmol) in dichloroethane (50 mL). Then the reaction mixture was refluxed for 2 h. After cooling, dichloromethane was added for dilution, the diluted product was respectively washed with 0.5N HCl (5 mL) and brine, the extract was dried with anhydrous magnesium sulfate and concentrated to obtain crude product A4-066 (250 mg), and the crude product was directly used for next reaction without purification. LCMS-ESI$^-$ (m/z): 310 (M−1).

Step 2

The crude product intermediate A4-066 (250 mg, 0.8 mmol) from step 1, 2,-(7-azobenzotriazole)-N,N,N',N'-tetramethylurea hexafluorophosphate (HATU, 380 mg, 1 mmol) and 2,4,6-triflurobenzylamine (161 mg, 1 mmol) were suspended in tetrahydrofuran (5 mL), and N,N-diisopropylethylamine (DIEPA, 200 mg, 1.6 mmol) was dropwise added at 0 V; after dropwise addition, the temperature was raised to 25° C., the reaction was performed for 2 h, then dichloromethane (50 mL) was added for dilution, the diluted product was respectively washed with 0.5N diluted hydrochloric acid and saturated saline solution, the extract was dried with anhydrous magnesium sulfate and concentrated to obtain the crude product A4-66 (280 mg). The crude product was directly used for next reaction without purification. LCMS-ESI$^-$ (m/z): 418 (M+1).

Step 3

Magnesium bromide (200 mg, 1.68 mmol) was added into the solution of the crude product intermediate A4-66 (380 mg, 0.6 mmol) from step 2 in acetonitrile (10 mL) at room temperature before the resulting mixture was stirred at 50° C. for 2 h. After the reaction mixture was stirred at 0° C., 0.5N diluted hydrochloric acid (10 mL) was added to make the mixture a solution. The resulting solution was diluted with water (50 mL) and extracted with dichloromethane (50 mL), the extract was dried with anhydrous magnesium sulfate and concentrated. The residue was purified by silica column chromatography (elution with a gradient of 0-5% methyl alcohol/dichloromethane) to provide the compound 66 (150 mg). $^1$H-NMR (400 MHz, CDCl$_3$) δ 11.82 (br, 1H), 10.39 (br, 1H), 8.43 (s, 1H), 7.30 (m, 2H), 6.99 (m, 2H), 5.20-5.09 (m, 2H), 4.65-4.45 (m, 2H), 4.21 (m, 1H), 4.11 (m, 1H), 3.32 (s, 1H), 2.86 (m, 1H), 1.48 (d, J=6.8 Hz, 3H). ESI$^+$ (m/z): 404 (M+1).

Example 21

Preparation of Compounds 73 and 74

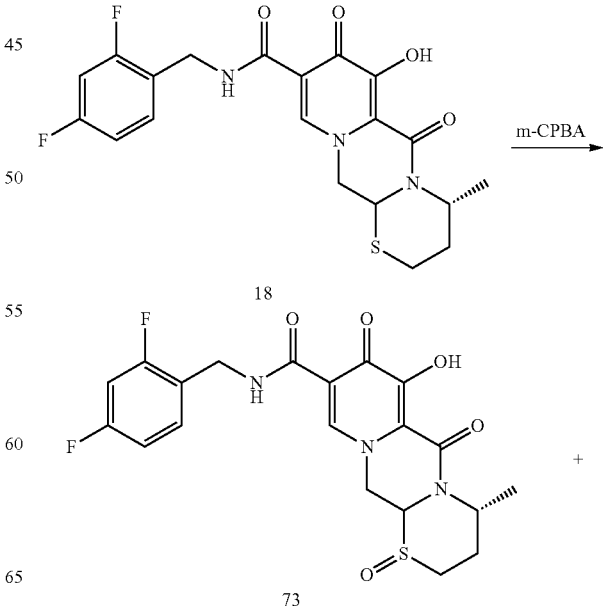

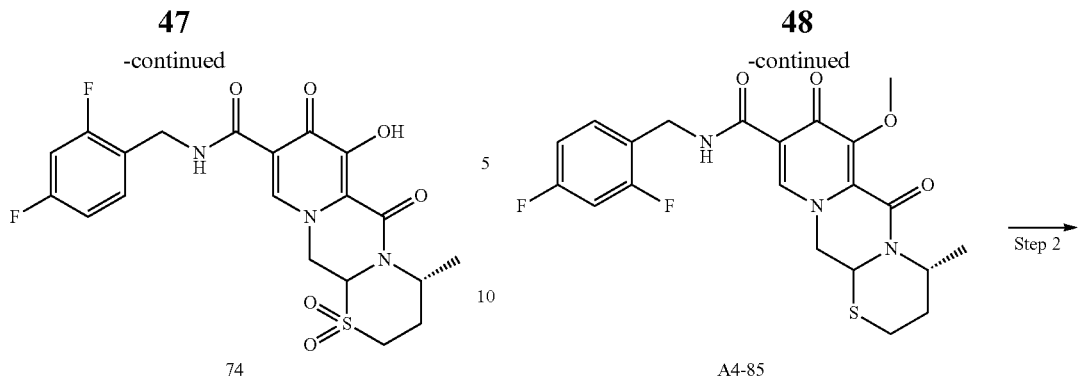

m-chloroperoxybenzoic acid (m-CPBA, 110 mg, 0.55 mmol) was added into the solution of compound 18 (220 mg, 0.5 mmol) in dichloromethane (10 mL). The reaction mixture was stirred at room temperature for 2 h, saturated sodium thiosulfate was added for quenching reaction, organic layer was separated, and the extract was dried with anhydrous magnesium sulfate and concentrated. The residue was purified by silica column chromatography (elution with a gradient of 0-5% methyl alcohol/dichloromethane) to provide the compound 73 (100 mg) and compound 74 (48 mg).

Compound 73

$^1$H-NMR (400 MHz, CDCl$_3$) δ 12.15 (br, 1H), 10.28 (br, 1H), 8.53 (s, 1H), 7.36 (m, 1H), 6.82 (m, 2H), 5.01-4.90 (m, 2H), 4.70-4.50 (m, 4H), 3.13 (m, 2H), 2.25 (m, 1H), 2.09 (m, 1H), 1.45 (d, J=6.8 Hz, 3H). ESI$^+$ (m/z): 452 (M+1).

Compound 74

$^1$H-NMR (400 MHz, CDCl$_3$) δ 12.45 (s, 1H), 10.42 (br, 1H), 8.48 (s, 1H), 7.35 (m, 1H), 6.81 (m, 2H), 5.29 (m, 2H), 4.80-4.60 (m, 5H), 2.95 (m, 2H), 2.21 (m, 1H), 2.05 (m, 1H), 1.42 (d, J=7.2 Hz, 3H). ESI$^+$ (m/z): 468 (M+1).

Example 22

Preparation of Compound 85

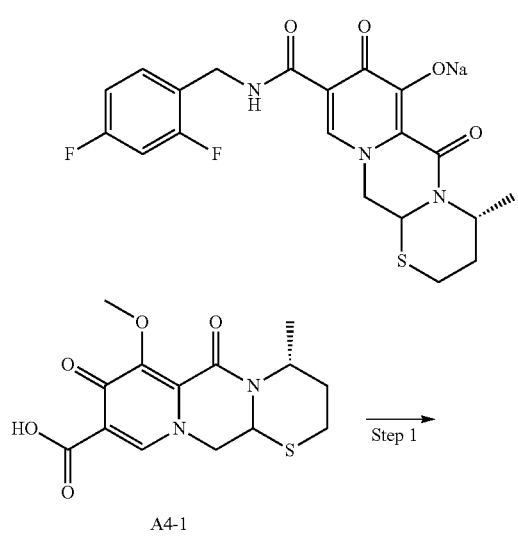

Step 1

The compound A4-1 (260 mg, 0.8 mmol), 2-(7-azobenzotriazole)-N,N,N',N'-tetramethylurea hexafluorophosphate (HATU, 380 mg, 1 mmol) and 2,4,6-triflurobenzylamine (161 mg, 1 mmol) were suspended in tetrahydrofuran (5 mL), and N,N-diisopropylethylamine (DIEPA, 200 mg, 1.6 mmol) was dropwise added at 0° C.; after dropwise addition, the temperature was raised to 25° C., the reaction was performed for 2 h, then dichloromethane (50 mL) was added for dilution, the diluted product was respectively washed with 0.5N diluted hydrochloric acid and saturated saline solution, the extract was dried with anhydrous magnesium sulfate and concentrated to obtain the crude product A4-85 (305 mg). $^1$H-NMR (400 MHz, CDCl$_3$) δ 10.44 (br, 1H), 8.42 (s, 1H), 7.37 (m, 1H), 6.82 (m, 2H), 5.18-5.09 (m, 2H), 4.64 (m, 2H), 4.48 (m, 1H), 4.15 (m, 1H), 4.06 (s, 3H), 3.22 (m, 1H), 2.68 (m, 1H), 2.10 (m, 1H), 1.81 (m, 1H), 1.37 (d, J=6.8 Hz, 3H). ESI$^+$ (m/z): 450 (M+1).

Step 2

Magnesium bromide (200 mg, 1.68 mmol) was added the solution of the compound A4-85 (305 mg, 0.65 mmol) into acetonitrile (10 mL) at room temperature before the resulting mixture was stirred at 50° C. for 2 h. After the reaction mixture was stirred at 0° C., 0.5N diluted hydrochloric acid (10 mL) was added to make the mixture a solution. The resulting solution was diluted with water (50 mL) and extracted with dichloromethane (50 mL), the extract was dried with anhydrous magnesium sulfate and concentrated. The residue was purified by silica column chromatography (elution with a gradient of 0-5% methyl alcohol/dichloromethane) to provide the compound 18 (200 mg). The compound 18 (90 mg, 0.2 mmol) was suspended in methanol (2 mL), then 0.1M sodium hydroxide-methanol solution (2 mL, 0.2 mmol) was added to be stirred for 30 min, methanol was removed by concentration to obtain a corresponding sodium salt, namely, compound 85 (94 mg), which was a light yellow solid. $^1$H-NMR (400 MHz, CDCl$_3$) δ 10.55 (br, 1H), 8.25 (br, 1H), 7.39 (m, 1H), 7.24 (m, 1H), 7.08 (m, 1H), 5.50 (m, 1H), 4.92 (m, 1H), 4.59-4.44 (m, 4H), 4.11 (d, J=13.6 Hz, 1H), 3.26 (m, 1H), 2.60 (m, 1H), 1.89-1.77 (m, 2H), 1.29 (d, J=6.8 Hz, 3H).

Example 23

Preparation of Compound 86

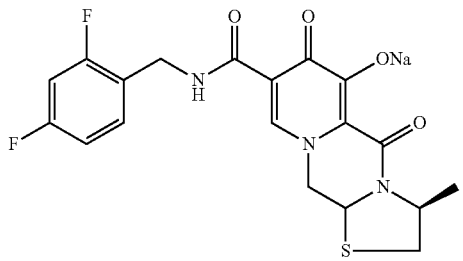

The compound 2 (82 mg, 0.2 mmol) was suspended in methanol (2 mL), then 0.1M sodium hydroxide-methanol solution (2 mL, 0.2 mmol) was added to be stirred for 30 min, then methanol was removed by concentration to obtain a corresponding sodium salt, namely, compound 86 (84 mg), which was a white-like solid. $^1$H-NMR (400 MHz, CDCl$_3$) δ 10.36 (br, 1H), 8.41 (s, 1H), 7.40 (m, 1H), 7.25 (m, 1H), 7.08 (m, 1H), 5.30 (m, 1H), 4.95 (m, 1H), 4.76 (m, 1H), 4.60 (m, 2H), 4.15 (m, 1H), 3.32 (m, 1H), 2.85 (m, 1H), 1.31 (d, J=6.4 Hz, 3H).

Experiment of In-Vitro Anti-HIV Activity in the Disclosure

Anti-HIV Activity of Compounds 1, 2, 3, 4, 5, 6, 8, 10, 12, 18, 20, 34 and 66 in Cell Culture I. Materials and Methods 1. Measurement of Drugs and Compounds To-be-detected samples are compounds 1, 2, 3, 4, 5, 6, 8, 10, 12, 18, 20, 34 and 66, and positive control compounds are tenofovir disoproxil fumarate (TDF) and dolutegravir. The to-be-detected samples are dissolved into DMSO, the concentration of stock solution is 50 mM, and storage condition is as follows: 4° C.; TDF and dolutegravir are dissolved into DMSO, the concentration of stock solution is 100 mM, and storage condition is 4° C.

2. Reagents and Solution (1) Reagents

MTT (3,(4,5-dimethylthiazol-2-yl)-2,5-diphenyl tetrazolium bromide), Triton X-100, Penicillin, sodium chloride, potassium chloride, potassium dihydrogen phosphate, disodium hydrogen phosphate, DMSO, anti-IgG Fc antibody, horseradish peroxidase (HRP) and labeled goat anti-rabbit IgG antibody are products from Sigma-aldrich company. SDS (sodium dodecyl sulfate) and Streptomycinsulfate are products from Amersco company. RPMI-1640 and fetal bovine serum are products from Invitrogen company, the anti-HIV p24 monoclonal antibody and the rabbit anti-HIV-1 p24 polyclonal antibody are prepared from this lab. MTT (3,(4,5-dimethylthiazol-2-yl)-2,5-diphenyl tetrazolium bromide), DMF (N, N'-dimethyl formamine), Penicillin and Streptomycin sulfate are all purchased from Sigma company. RPMI-1640 and fetal bovine serum are products from Gibco company.

(2) A RPMI-1640 complete culture medium contains 10% fetal bovine serum, 2 mML-glutamine, 10 mM HEPES, 50 μM-2-mercaptoethanol, 100,000 IU Penicillin and 100 μg/ml Streptomycin.

3. Cells and Viruses

Human T lymphocytic series C8166 and HIV-1 experiment strain HIV-1IIIB are both from National Institutes of Health (NIH); cells are cultured in the RPMI-1640 complete culture medium containing 10% fetal bovine serum. HIV-1IIIB is prepared by using a conventional method, titration and calculation of TCID 50 of viruses are performed. Virus stock solution is subpackaged and stored at −70° C. Cells and viruses are cryopreserved and recovered according to conventional methods.

4. Infectious Titration of HIV-1

HIV-1IIIB is titrated by the improved method described by Johnson & Byington (1990). It is briefly described as follows: the HIV-1 stock solution is diluted by 4 times on a 96-well plate with 10 gradients and 6 repetition wells per gradient, and 6 control wells are set at the same time. 50 μl of C8166 cells are added in each well, the final volume of each well is 200 μl. Culture is performed under the conditions of 37° C. and 5% CO$_2$. 100 μl of fresh RPMI-1640 complete medium is supplemented on the 3rd day. The cytopathic effect (CPE) induced by HIV is observed under the inverted microscope on the 7th day, which is determined depending on whether syncytiums are present in each well. TCID 50 (50% tissue culture infection dose) of viruses is calculated according to the Reed & Muench method.

5. Measurement of HIV-1 p24 Antigen with p24 Antigen Capture ELISA Method

The 1 μg/plate of anti-mouse IgG Fc antibody was paved at 4° C. for overnight; the plate was sealed with 5% skimmed milk powder 4° C. for overnight; 100 μl/well mouse anti-p24 monoclonal antibody was added at 37° C. for 1 h; 100 μl/well (1:100) diluted rabbit anti-p24 polyclonal antibody (homemade) was added for 1 h at 37° C.; 100 μl/well (1:20000) diluted goat anti-rabbit IgG HRP was added for 1 h at 37° C.; OPD substrate reaction solution was added. After 10 min, 2M sulfuric acid was added to stop the reaction. The OD value was determined by Elx800 ELISA, and the wavelength was measured as 490/630 nm. The inhibition rate and EC50 of the drug on the p24 antigen replication and expression of HIV-1, namely, the concentration of the drug inhibiting 50% HIV-1 p24 antigen were calculated, namely, the concentration of the drug inhibiting 50% HIV-1 p24 antigen expression was calculated.

6. Toxicity Test of C8166 Cells

100 μl of 4×10$^5$ ml C8166 was mixed with different to-be-detected drug solutions, and 3 repetition wells were set. Meanwhile, control wells were set. Culture was performed for 3 days under the conditions of 37° C. and 5% CO$_2$. Cytotoxicity was detected with MTT colorimetric method. The OD value was measured with EL ×800 ELIASA, the wavelength was measured as 570/630 nm. The CC50 value was calculated (50% cytotoxic concentration), namely, the concentration of the drug when toxicity was generated for 50% normal T lymphocytic series C8166.

7. Inhibition Experiment for Cytopathic Effect (CPE) of HIV-1IIIB

8×10$^5$/ml C8166 cells were inoculated onto the 96-well cell culture plate containing 100 μl/well drug subjected to gradient multiple proportion dilution in an amount of 50 μl/well, and then 50 μl HIV-1IIIB was added to dilute the supernatant, 1300 TCID 50/well. 3 repetition wells were set. Meanwhile, normal cell control wells without drugs were set. TDF and dolutegravir were positive drug controls. Culture was performed for 3 days under the conditions of 37° C. and 5% CO$_2$, and syncytia formation were counted under the inverted microscope (100×). EC50 (50% Effective Concentration) is the concentration of the drug when 50% of syncytia formation is inhibited.

8. Inhibition Effect of Samples on Replication in Experiment Strain HIV-1IIIB Acute Infectious C8166 Cells 4×105 cells/ml C8166 cells and HIV-1IIIB MOI (multiplicity of infection=0.04) are infected for 2 h at 37° C., the obtained mixture is washed three times with PBS to remove free virus ions, 100 μl of cells are inoculated onto the 96-well plate containing 100 μl of to-be-detected compounds having different dilutions and cultured for 3 days under the conditions of 37° C. and 5% $CO_2$. The cultural supernatant is centrifuged and then collected, and finally lysed and inactivated with 0.5% Triton X-100. The inhibition effect of the drug on HIV-1 replication is detected by using the p24 antigen capture ELISA method.

9. Calculation Formula

According to experiment results, fitted curves are drawn using Origin2016, the 50% effective concentrations (EC50) of the samples inhibiting viruses, 50% cell growth inhibition concentrations (CC50) and TI (therapeutic index) value against HIV-1 activity are calculated based on Reed & Muench method, and the TI value is TI=CC50/EC50.

1. Cell growth survival rate (%)=experiment well OD value/control well OD value×100

2. HIV-1 cytopathic cell inhibition rate (%)=(1−experiment well syncytia number/control well syncytia number)×100

3. HIV-1 p24 antigen expression inhibition rate (%)=(1−experiment well OD value/control well OD value)×100

Inhibition Effects of Compounds 1, 2, 3, 4, 5, 6, 8, 10, 12, 18, 20, 34 and 66 on HIV-1 in C8166 Cell Culture Toxicities and anti-HIV-1 activities of compounds 1, 2, 3, 4, 5, 6, 8, 10, 12, 18, 20, 34 and 66 on cells are measured with MTT method. Results are seen in Table 1.

TABLE 1

In-vitro cytotoxicity and anti-HIV-1 activity of compounds of the disclosure and positive drugs TDF and Dolutegravir

| Compounds | Experiments | Methods | CC50 (μM) | EC50 | Therapeutic index TI |
|---|---|---|---|---|---|
| TDF | Cytotoxicity experiment | MTT | 157.14 ± 21.39 | | |
| | Inhibition experiment of HIV-1IIIB cytopathy | cpe | | 12.06 ± 11.27 nM | 13029.85 |
| | Inhibition experiment of HIV-1IIIB acute infectious C8166 cells | P24 | | 8.07 ± 4.72 nM | 19472.12 |
| Dolutegravir | Cytotoxicity experiment | MTT | 26.55 ± 2.20 | | |
| | Inhibition experiment of HIV-1IIIB cytopathy | cpe | | 2.13 ± 0.33 nM | 12464.48 |
| | Inhibition experiment of HIV-1IIIB acute infectious C8166 cells | P24 | | 1.05 ± 0.12 nM | 25285.71 |
| 1 | Cytotoxicity experiment | MTT | 20.33 ± 0.21 | | |
| | Inhibition experiment of HIV-1IIIB cytopathy | cpe | | 186.56 ± 31.10 pM | 108973.00 |
| | Inhibition experiment of HIV-1IIIB acute infectious C8166 cells | P24 | | 200.78 ± 33.32 pM | 101255.11 |
| 2 | Cytotoxicity experiment | MTT | 11.33 ± 0.11 | | |
| | Inhibition experiment of HIV-1IIIB cytopathy | cpe | | 15.66 ± 2.61 pM | 723499.36 |
| | Inhibition experiment of HIV-1IIIB acute infectious C8166 cells | P24 | | 18.06 ± 2.86 pM | 6273353.27 |
| 3 | Cytotoxicity experiment | MTT | 18.63 ± 0.35 | | |
| | Inhibition experiment of HIV-1IIIB cytopathy | cpe | | 28.88 ± 5.11 pM | 645083.10 |
| | Inhibition experiment of HIV-1IIIB acute infectious C8166 cells | P24 | | 35.06 ± 6.02 pM | 531374.79 |
| 4 | Cytotoxicity experiment | MTT | 18.63 ± 0.35 | | |
| | Inhibition experiment of HIV-1IIIB cytopathy | cpe | | 28.88 ± 5.11 pM | 645083.10 |
| | Inhibition experiment of HIV-1IIIB acute infectious C8166 cells | P24 | | 35.06 ± 6.02 pM | 531374.79 |
| 5 | Cytotoxicity experiment | MTT | 16.13 ± 0.30 | | |
| | Inhibition experiment of HIV-1IIIB cytopathy | cpe | | 162.00 ± 18.11 pM | 99567.90 |
| | Inhibition experiment of HIV-1IIIB acute infectious C8166 cells | P24 | | 188.06 ± 22.78 pM | 85770.50 |
| 6 | Cytotoxicity experiment | MTT | 22.63 ± 0.48 | | |
| | Inhibition experiment of HIV-1IIIB cytopathy | cpe | | 182.00 ± 20.33 pM | 124340.07 |
| | Inhibition experiment of HIV-1IIIB acute infectious C8166 cells | P24 | | 208.06 ± 36.12 pM | 108766.70 |

TABLE 1-continued

In-vitro cytotoxicity and anti-HIV-1 activity of compounds of the disclosure and positive drugs TDF and Dolutegravir

| Compounds | Experiments | Methods | CC50 (μM) | EC50 | Therapeutic index TI |
|---|---|---|---|---|---|
| 8 | Cytotoxicity experiment | MTT | 26.33 ± 0.35 | | |
| | Inhibition experiment of HIV-1IIIB cytopathy | cpe | | 715.76 ± 102.61 pM | 36786.07 |
| | Inhibition experiment of HIV-1IIIB acute infectious C8166 cells | P24 | | 780.96 ± 112.86 pM | 33714.91 |
| 10 | Cytotoxicity experiment | MTT | 45.16 ± 0.41 | | |
| | Inhibition experiment of HIV-1IIIB cytopathy | cpe | | 3.82 ± 0.51 nM | 11822.00 |
| | Inhibition experiment of HIV-1IIIB acute infectious C8166 cells | P24 | | 4.16 ± 0.58 nM | 10855.77 |
| 12 | Cytotoxicity experiment | MTT | 28.63 ± 0.32 | | |
| | Inhibition experiment of HIV-1IIIB cytopathy | cpe | | 526.23 ± 77.12 pM | 54405.86 |
| | Inhibition experiment of HIV-1IIIB acute infectious C8166 cells | P24 | | 589.06 ± 86.06 pM | 48558.34 |
| 18 | Cytotoxicity experiment | MTT | 14.03 ± 0.21 | | |
| | Inhibition experiment of HIV-1IIIB cytopathy | cpe | | 10.16 ± 2.11 pM | 1380633.73 |
| | Inhibition experiment of HIV-1IIIB acute infectious C8166 cells | P24 | | 11.09 ± 2.09 pM | 1265674.33 |
| 20 | Cytotoxicity experiment | MTT | 18.33 ± 0.19 | | |
| | Inhibition experiment of HIV-1IIIB cytopathy | cpe | | 125.06 ± 17.03 pM | 146569.64 |
| | Inhibition experiment of HIV-1IIIB acute infectious C8166 cells | P24 | | 148.46 ± 20.12 pM | 123467.60 |
| 34 | Cytotoxicity experiment | MTT | 20.68 ± 0.32 | | |
| | Inhibition experiment of HIV-1IIIB cytopathy | cpe | | 35.88 ± 6.11 pM | 576365.66 |
| | Inhibition experiment of HIV-1IIIB acute infectious C8166 cells | P24 | | 38.13 ± 6.52 pM | 542355.51 |
| 66 | Cytotoxicity experiment | MTT | 20.08 ± 0.21 | | |
| | Inhibition experiment of HIV-1IIIB cytopathy | cpe | | 75.35 ± 8.61 pM | 266489.71 |
| | Inhibition experiment of HIV-1IIIB acute infectious C8166 cells | P24 | | 83.56 ± 10.86 pM | 240306.37 |

It can be seen from Table 1 that novel sulfur-containing polycyclic-hydroxypyridone carboxamide analogs have good anti-HIV activity, and in particular, compounds 2, 18 and 34 have extremely strong inhibition effects on HIV-1 replication in vitro and possess a good application development prospect. Development of this type of compounds is of great significance on the development of AIDS drugs, and will bring good news for AIDS patients.

The above descriptions are only partial preferred embodiments of the disclosure, the disclosure is not limited to contents of these embodiments. Those skilled in the art can make various variations and changes within the conception range of the technical solution of the disclosure, and the made any variations and changes are all included within the protection scope of the disclosure.

We claim:

1. A compound represented by the following formula (I) or a stereoisomer thereof or a pharmaceutically acceptable salt thereof:

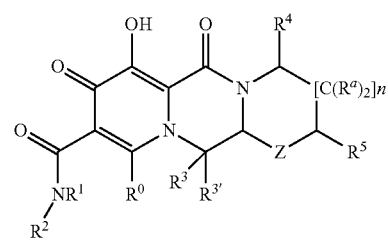

wherein, Z is selected from S, SO and SO$_2$;

R$^0$ is hydrogen, halogen, hydroxyl, a lower alkyl or a lower alkenyl, wherein each of the lower alkyl and the lower alkenyl is optionally interrupted by heteroatoms selected from —O—, —S—, —S(O)—, —S(O)$_2$—, and —NR$^6$—; —R$^6$— is hydrogen, a lower alkyl, a cycloalkyl, a cycloalkyl lower alkyl, a lower alkenyl, a lower alkoxy, a aryl, an aryl lower alkyl, an aryloxy, an epoxy group, hydroxyl, an amino, and a phosphate group;

Each $R^a$ is independently hydrogen, halogen, a lower alkyl, a cycloalkyl, a cycloalkyl lower alkyl, a lower alkenyl, a lower alkoxy, an aryl, an aryl lower alkyl, an aryloxy, and an epoxy group;

n is an integer of 0~8; when n is 0, the ring is a five-membered ring;

$R^1$ is hydrogen, a lower alkyl, a cycloalkyl, a cycloalkyl lower alkyl, a lower alkenyl, a lower alkoxy, a aryl, a aryl lower alkyl, a aryloxy, and an epoxy group;

$R^2$ is hydrogen, a lower alkyl, a cycloalkyl, a cycloalkyl lower alkyl, a lower alkenyl, a lower alkoxy, an aryl, an aryl lower alkyl, an aryloxy, and an epoxy group;

$R^3$ and $R^{3'}$ are each independently hydrogen, a lower alkyl, a cycloalkyl, a cycloalkyl lower alkyl, a lower alkenyl, a lower alkoxy, an aryl, an aryl lower alkyl, an aryloxy, an epoxy group, hydroxyl, an amino, and a phosphate group;

$R^4$ and $R^5$ are each independently hydrogen or a lower alkyl, a cycloalkyl, a cycloalkyl lower alkyl, a lower alkenyl, a lower alkoxy, a aryl, an aryl lower alkyl, an aryloxy, and a heterocycle;

or wherein $R^4$ and $R^5$ are combined together to form —W—, wherein W is $[C(R^6)_2]_L$ (L is an integer of 1~4);

each $R^6$ is independently hydrogen, halogen, a lower alkyl, a cycloalkyl, a cycloalkyl lower alkyl, a lower alkenyl, a lower alkoxy, an aryl, an aryl lower alkyl, an aryloxy, and an epoxy group.

2. The compound according to claim 1, comprising a compound represented by the following formula (I-A) or a stereoisomer thereof or a pharmaceutically acceptable salt thereof:

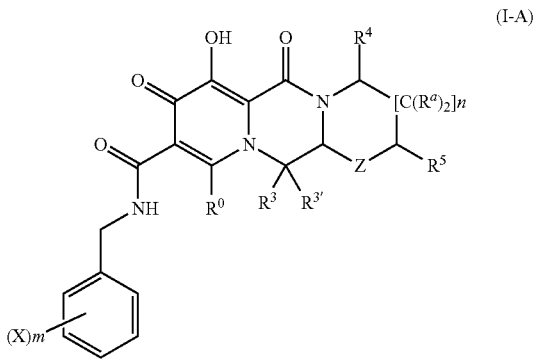

(I-A)

wherein, Z is selected from S, SO and $SO_2$;

each X is independently hydrogen, halogen, hydroxyl, a lower alkyl, a cycloalkyl, a cycloalkyl lower alkyl, a lower alkenyl, a lower alkoxy, an aryl, an aryl lower alkyl, an aryloxy, an epoxy group, hydroxyl, an amino, and a phosphate group;

m is an integer of 0~3;

when m is 1, X is halogen, fluoro in the 2-position or 4-position of the benzene ring;

when m is 2, X is halogen; fluoro in the 2-position and the 4-position of the benzene ring, fluoro in the 2-position and the 3-position of the benzene ring, fluoro in the 2-position and the 6-position of the benzene ring, fluoro in the 3-position and the 4-position of the benzene ring, fluoro in the 3-position and chloro in the 4-position of the benzene ring, fluoro in the 2-position and chloro in the 4-position of the benzene ring, or chloro in the 2-position and fluoro in the 4-position of the benzene ring;

when m is 3, X is halogen; fluoro in the 2-position, 4-position and 6-position or 2-position, 3-position and 4-position of the benzene ring.

3. The compound according to claim 1, comprising a compound represented by the following formula (I-B) or a stereoisomer thereof or a pharmaceutically acceptable salt thereof:

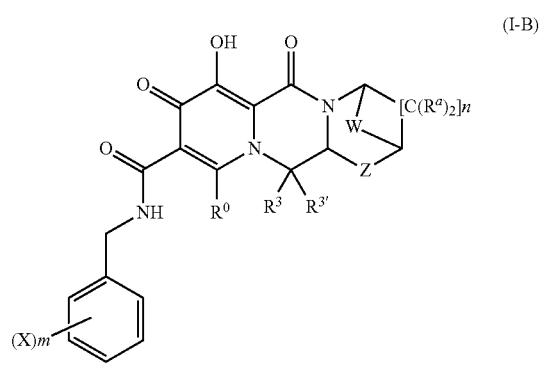

(I-B)

wherein, Z is selected from S, SO and $SO_2$;

W is $[C(R^6)_2]_L$ (L is an integer of 1~4); wherein, each $R^6$ is independently hydrogen, halogen, a lower alkyl, a cycloalkyl, a cycloalkyl lower alkyl, a lower alkenyl, a lower alkoxy, an aryl, an aryl lower alkyl, an aryloxy and an epoxy group;

each X is independently hydrogen, halogen, hydroxyl, a lower alkyl, a cycloalkyl, a cycloalkyl lower alkyl, a lower alkenyl, a lower alkoxy, an aryl, an aryl lower alkyl, an aryloxy, an epoxy group, a hydroxyl, an amino, and a phosphate group;

m is an integer of 0~3;

when m is 1, X is halogen; fluoro in the 2-position or 4-position of the benzene ring;

when m is 2, X is halogen; fluoro in the 2-position and the 4-position of the benzene ring, fluoro in the 2-position and the 3-position of the benzene ring, fluoro in the 2-position and the 6-position of the benzene ring, fluoro in the 3-position and the 4-position of the benzene ring, fluoro in the 3-position and chloro in the 4-position of the benzene ring, fluoro in the 2-position and chloro in the 4-position of the benzene ring, or chloro in the 2-position and fluoro in the 4-position of the benzene ring;

when m is 3, X is halogen; fluoro in the 2-position, 4-position and 6-position or the 2-position, 3-position and 4-position of the benzene ring.

4. The compound according to claim 1, comprising a compound represented by the following formula (I-C) or a stereoisomer thereof or a pharmaceutically acceptable salt thereof:

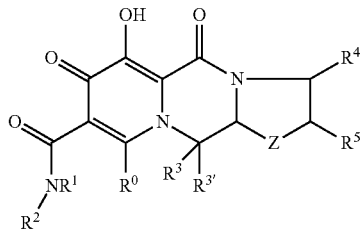

(I-C)

wherein, Z is selected from S, SO and SO$_2$.

5. The compound according to claim 1, comprising a compound represented by the following formula (I-D) or a stereoisomer thereof or a pharmaceutically acceptable salt thereof:

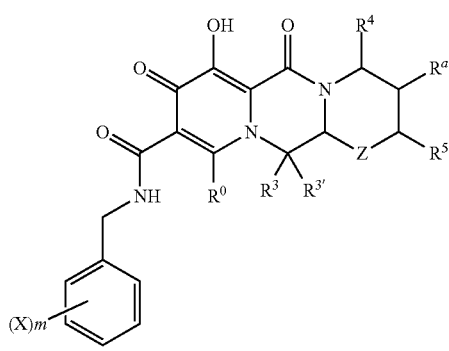

(I-D)

wherein, Z is selected from S, SO and SO$_2$, each X is independently hydrogen, halogen, hydroxyl, optionally substituted lower alkyl, a cycloalkyl, a cycloalkyl lower alkyl, a lower alkenyl, a lower alkoxy, an aryl, an aryl lower alkyl, an aryloxy, an epoxy group, hydroxyl, an amino, and a phosphate group;

m is an integer of 0-3;

when m is 1, X is halogen; fluoro in the 2-position or 4-position of the benzene ring;

when m is 2, X is halogen; fluoro in the 2-position and the 4-position of the benzene ring, fluoro in the 2-position and the 3-position of the benzene ring, fluoro in the 2-position and the 6-position of the benzene ring, fluoro in the 3-position and the 4-position of the benzene ring, fluoro in the 3-position and chloro in the 4-position of the benzene ring, fluoro in the 2-position and chloro in the 4-position of the benzene ring, or chloro in the 2-position and fluoro in the 4-position of the benzene ring;

when m is 3, X is halogen; fluoro in the 2-position, 4-position and 6-position or the 2-position, 3-position and 4-position of the benzene ring.

6. The compound according to claim 1 selected from the group consisting of: compound A3, compound A6, compound A7, a stereoisomer of the compound, and a pharmaceutically acceptable salt thereof:

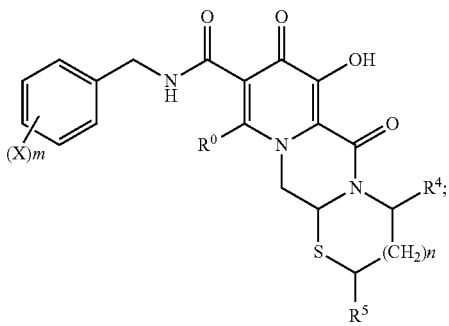

A3

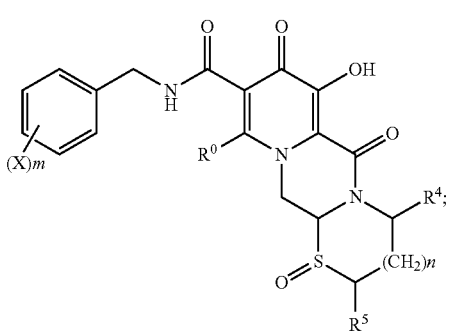

A6

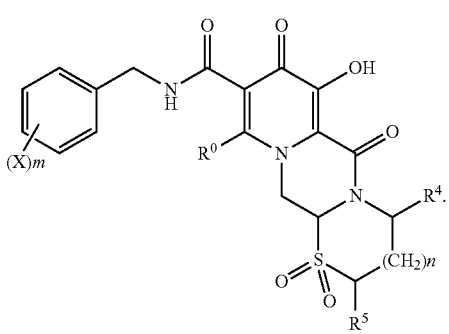

A7

7. The compound according to claim 1 selected from the group consisting of: 1-93, enantiomers thereof; diastereomers thereof; a mixture of diastereomers thereof; a mixture of diastereomers thereof; a mixture of enantiomers and diastereomers thereof; and a pharmaceutically acceptable salt thereof;

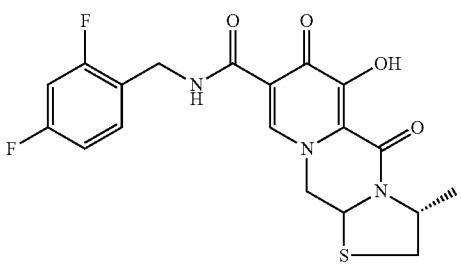

1

| 59 -continued | | 60 -continued | |
|---|---|---|---|
| 2 | 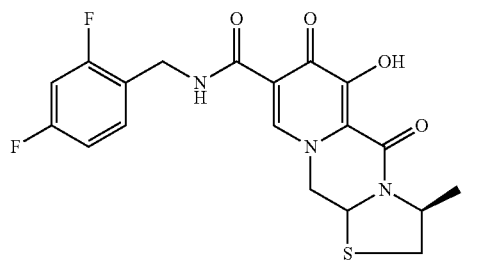 | 8 | 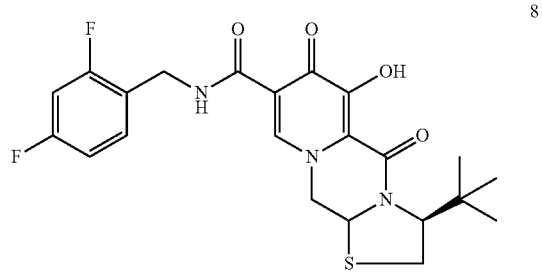 |
| 3 | 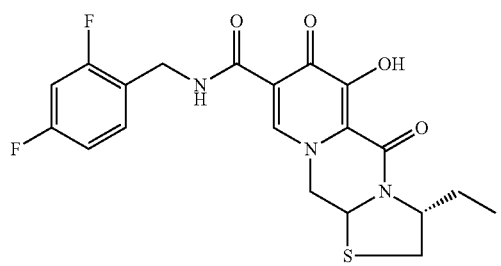 | 9 | 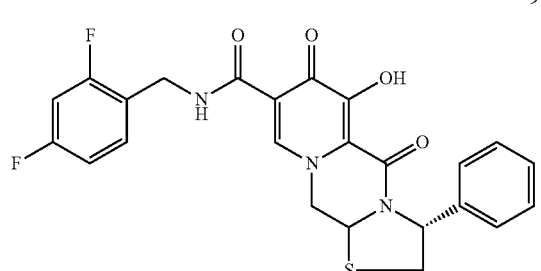 |
| 4 | 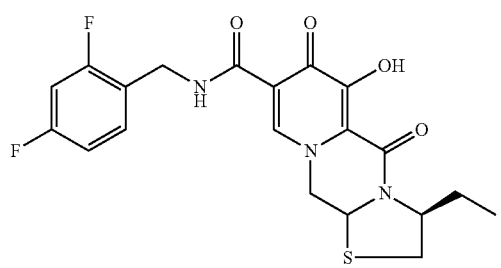 | 10 | 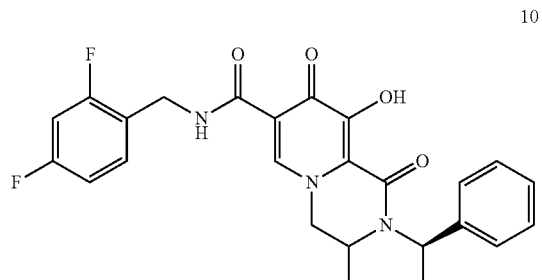 |
| 5 | 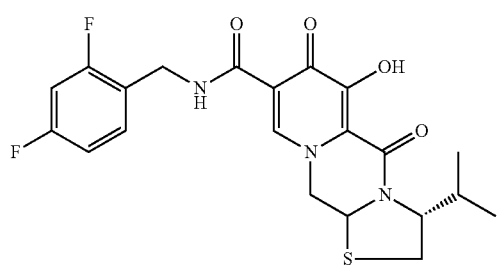 | 11 | 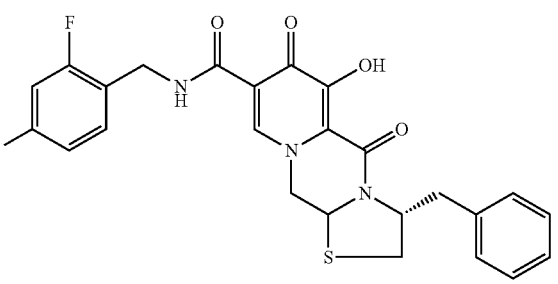 |
| 6 | 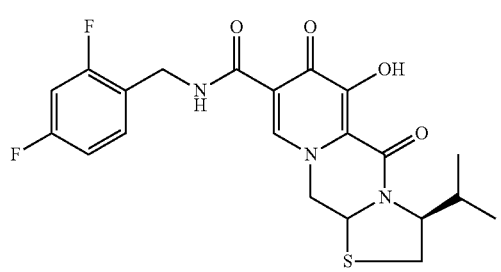 | 12 | 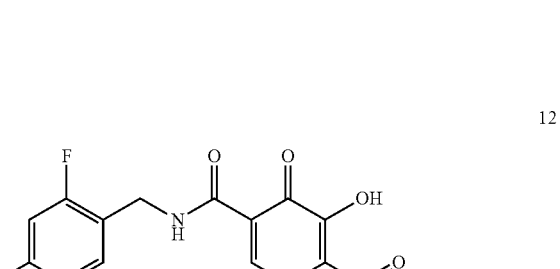 |
| 7 | 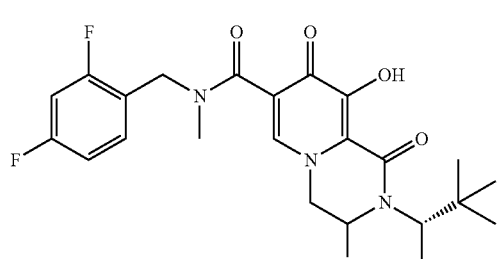 | | 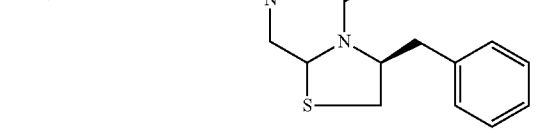 |

13
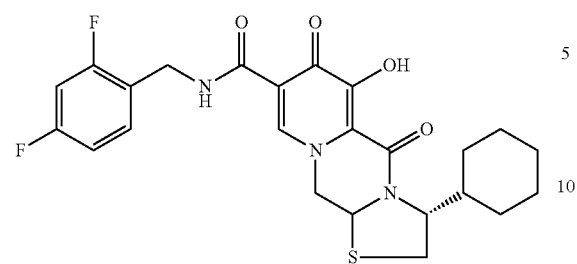
14
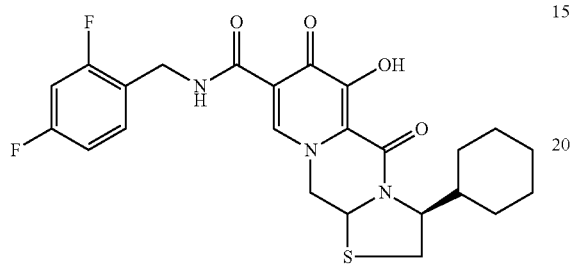
15
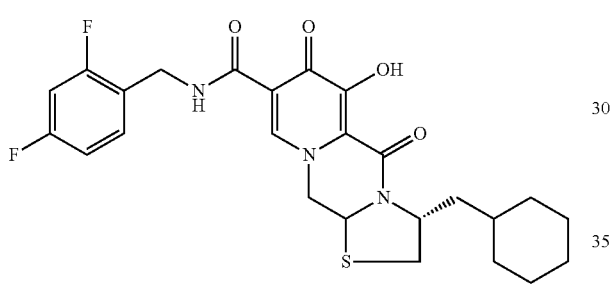
16
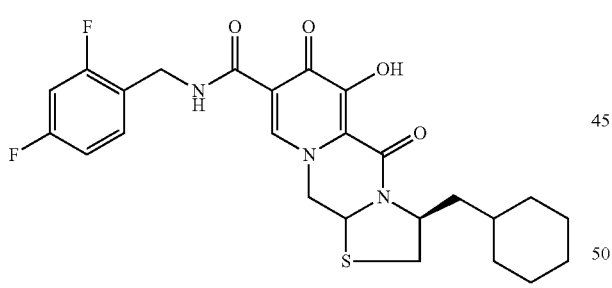
17
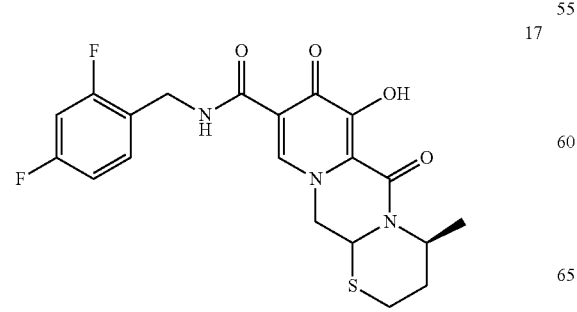
18
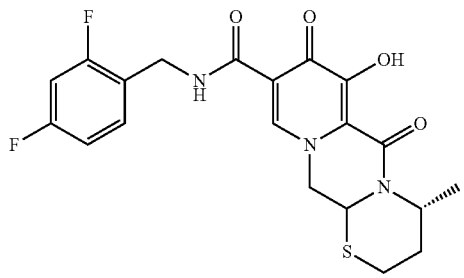
19
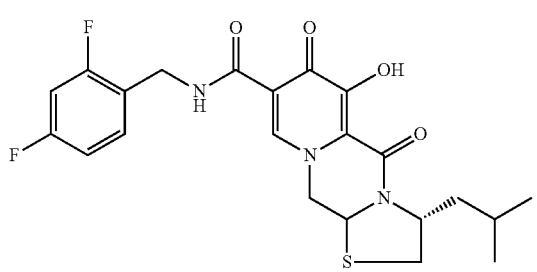
20
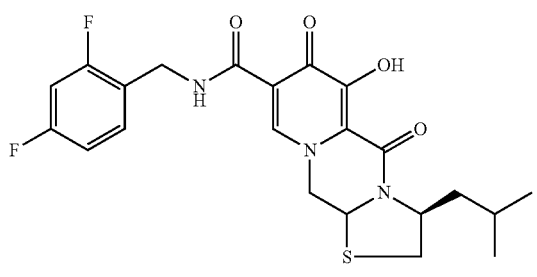
21
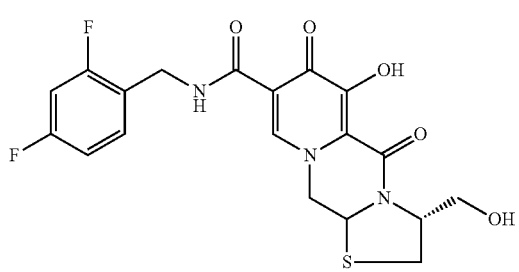
22
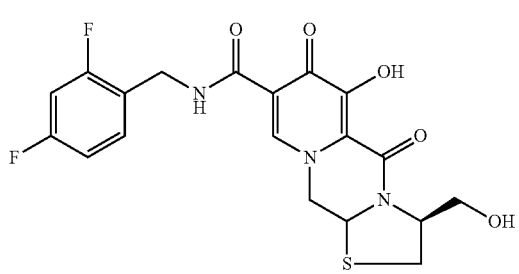

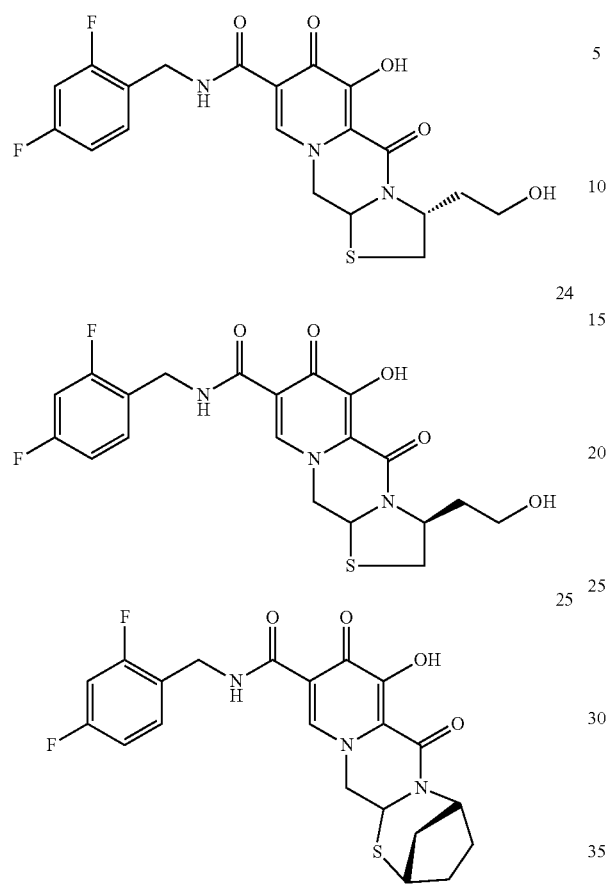
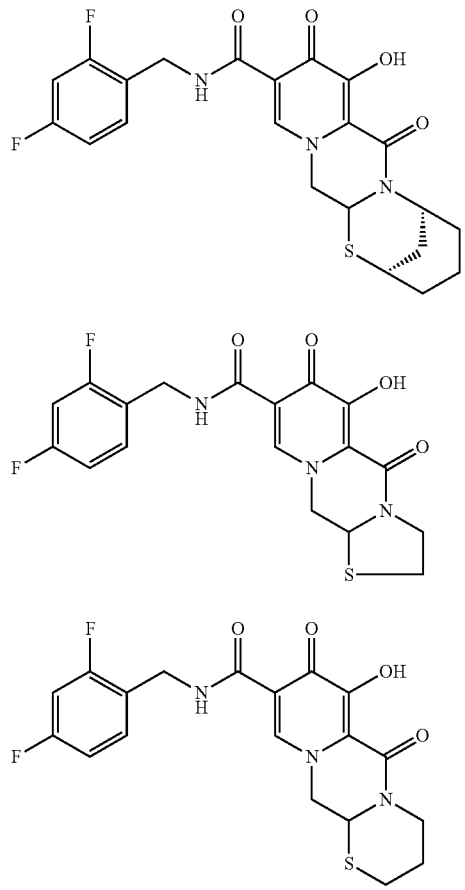
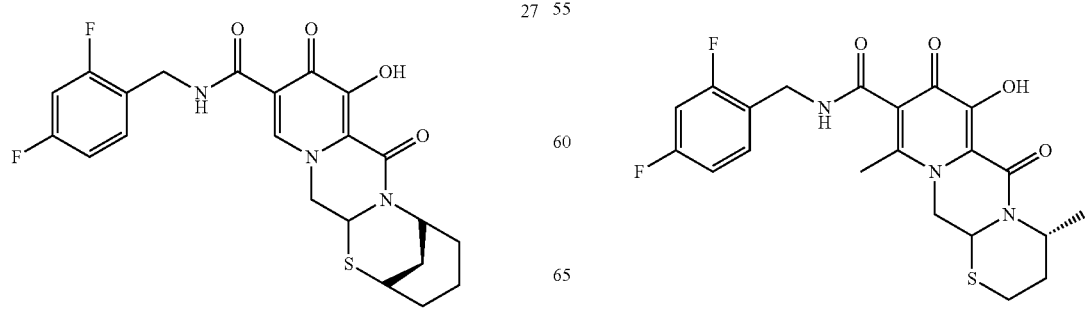

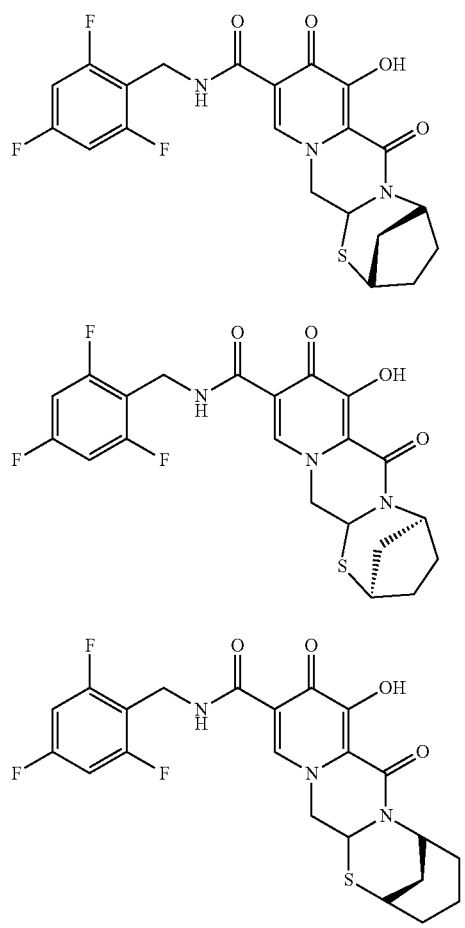
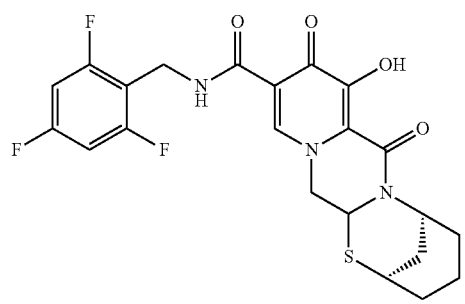
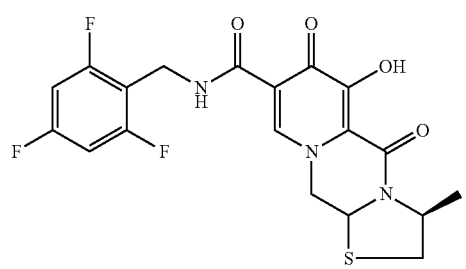
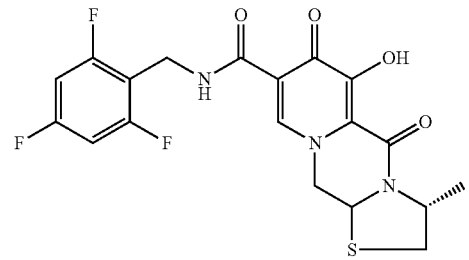
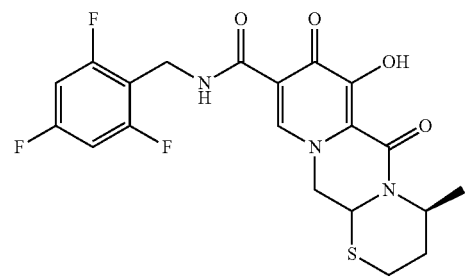
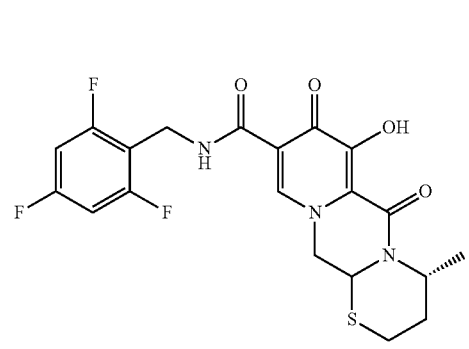
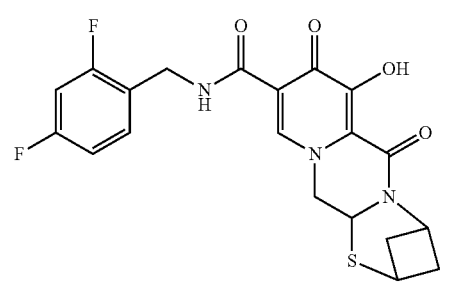
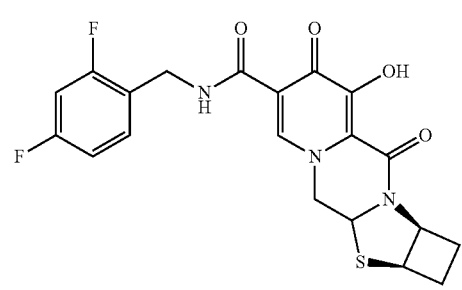

67
-continued
43
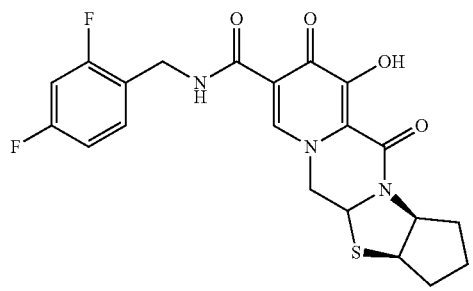
44
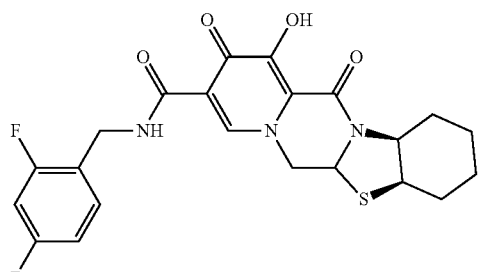
45
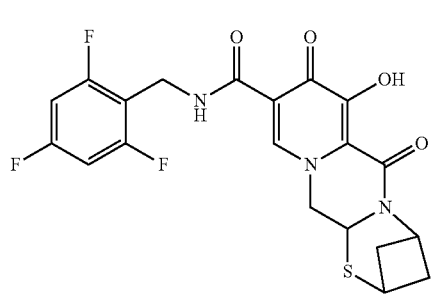
46
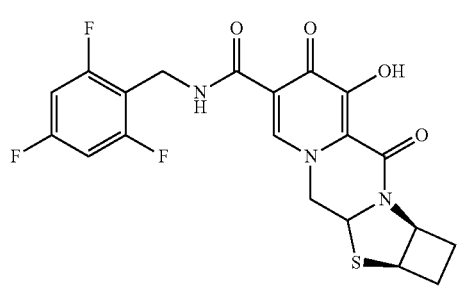
47
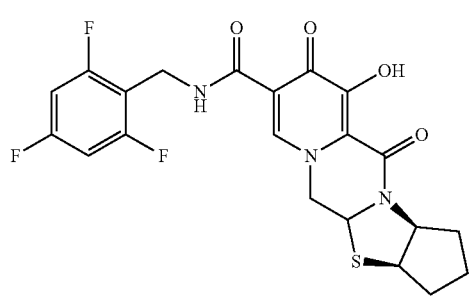
68
-continued
48
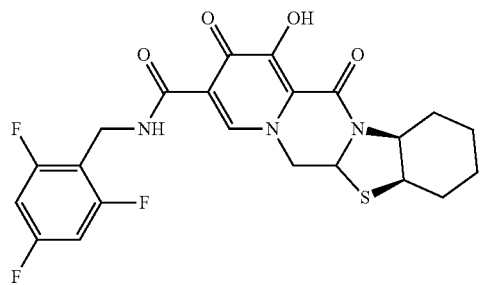
49
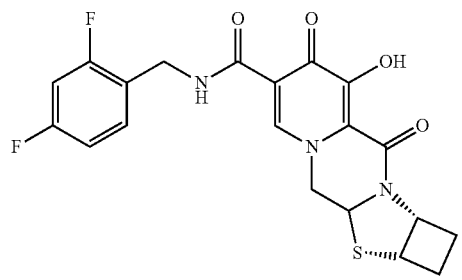
50
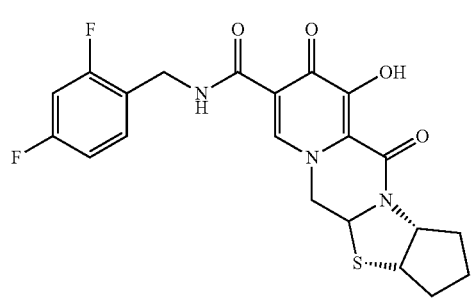
51
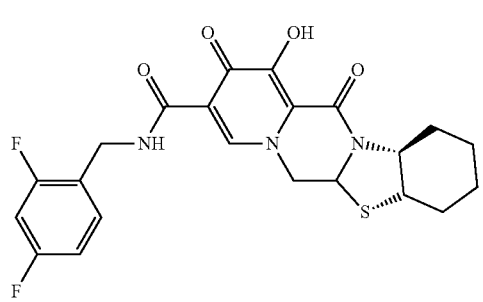
52
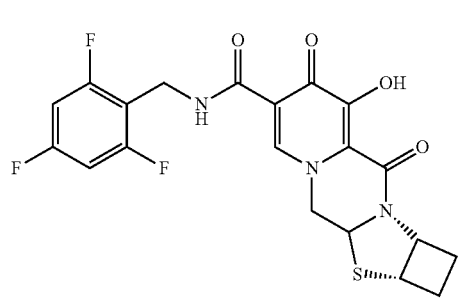

| 69 | 70 |
|---|---|
| -continued | -continued |
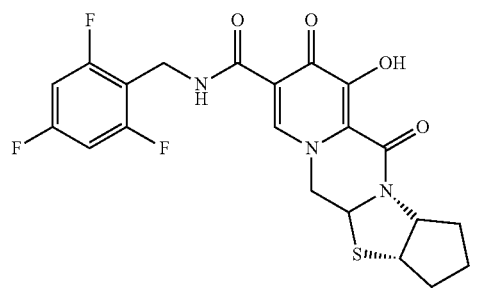
53
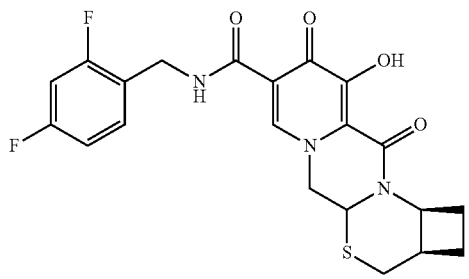
58
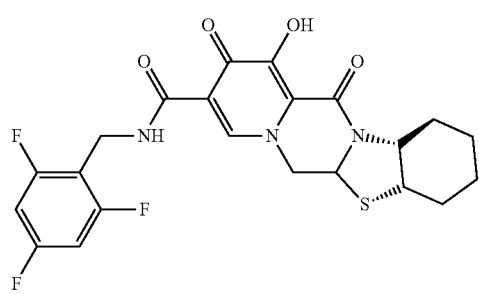
54
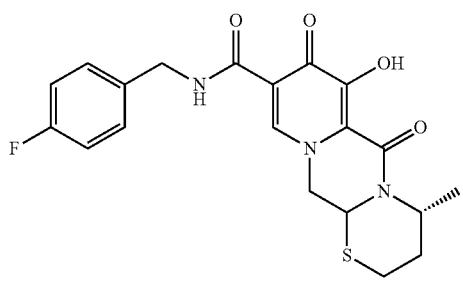
59
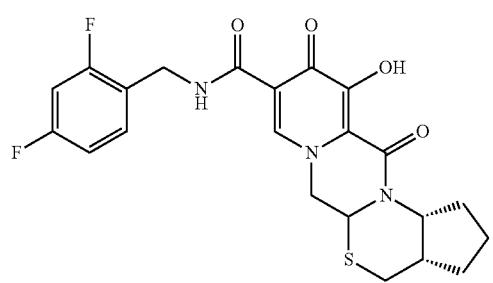
55
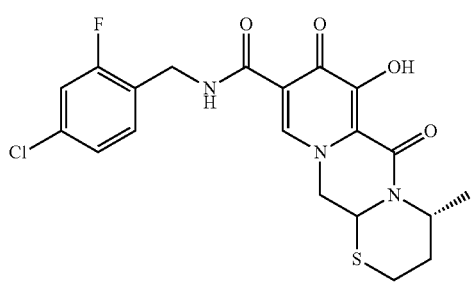
60
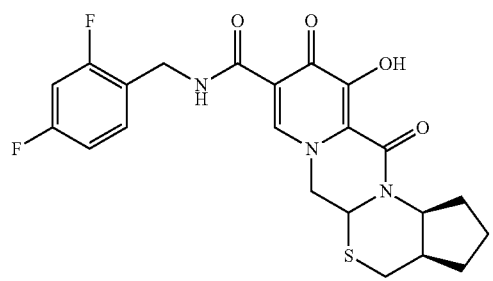
56
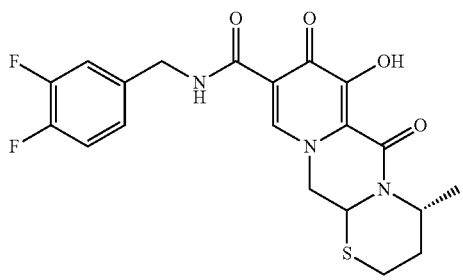
61
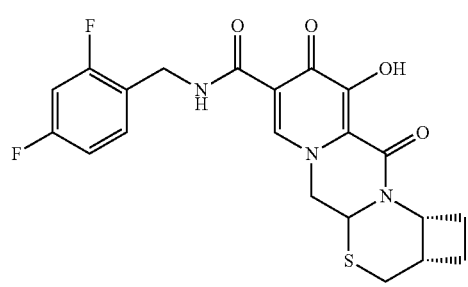
57
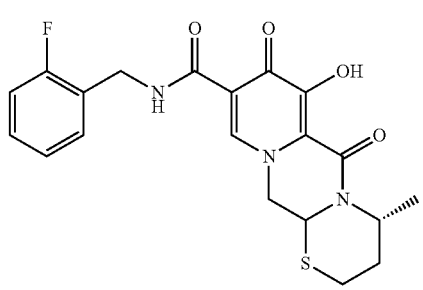
62

63
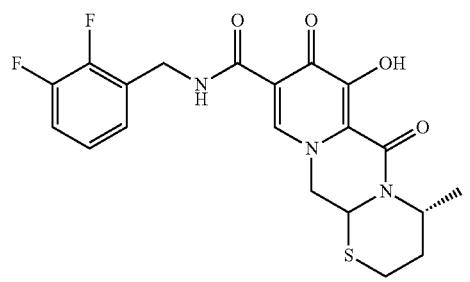
64
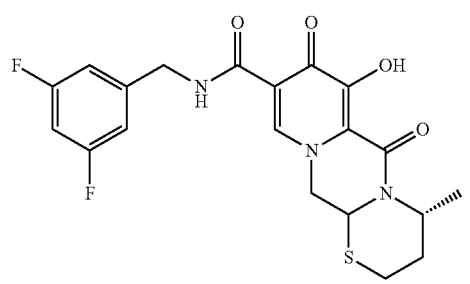
65
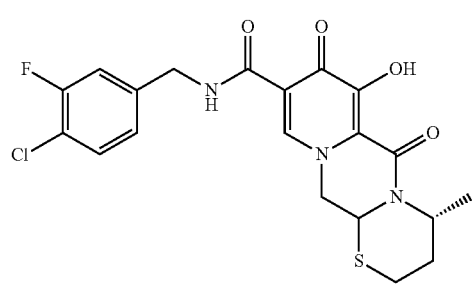
66
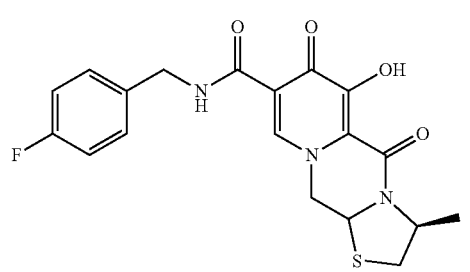
67
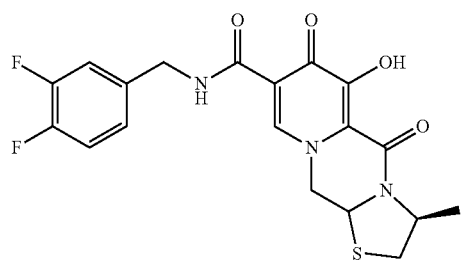
68
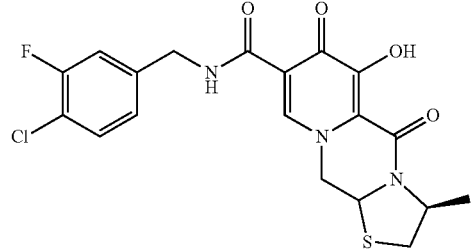
69
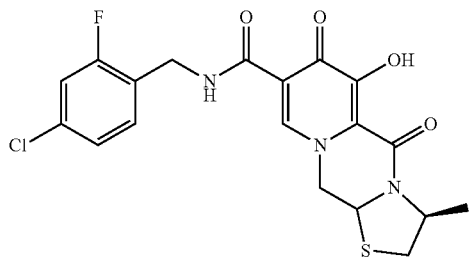
70
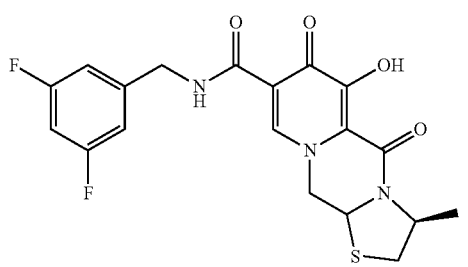
71
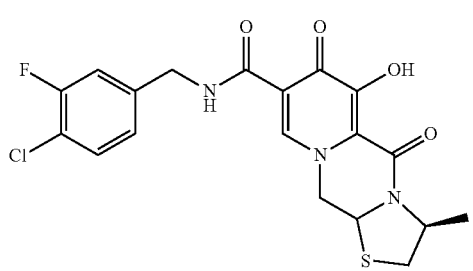
72
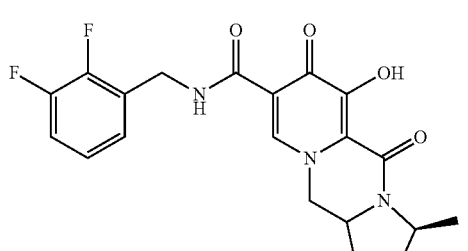
73
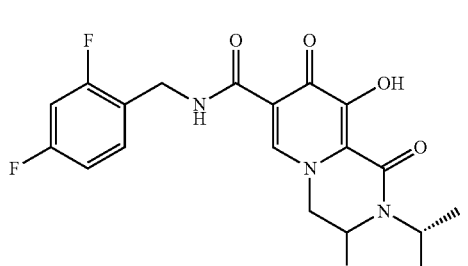
74
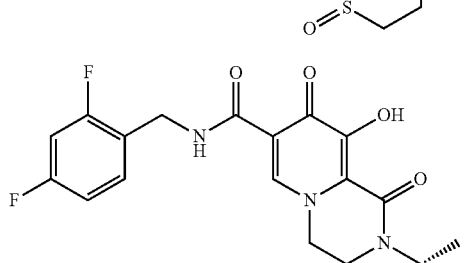

75
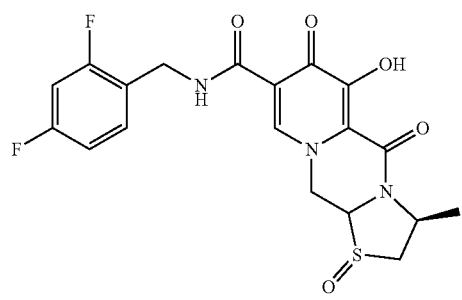
76
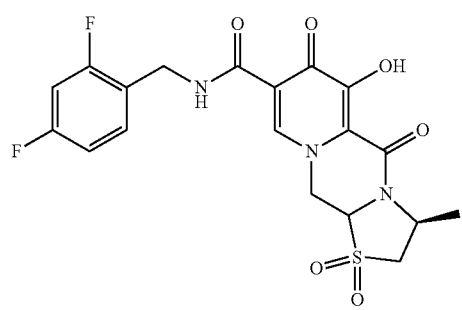
77
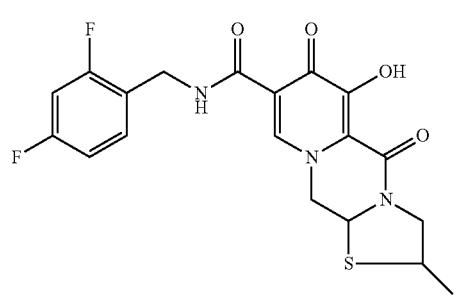
78
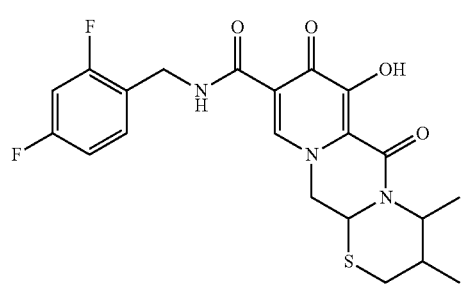
79
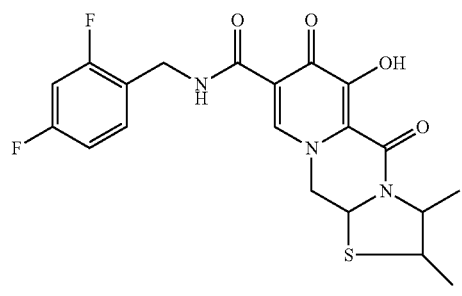
80
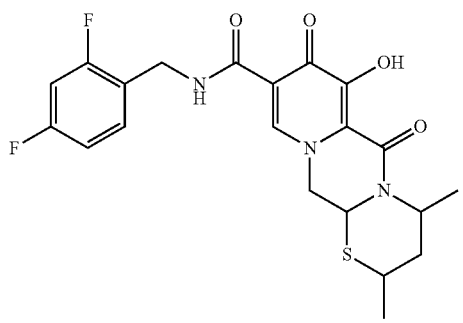
81
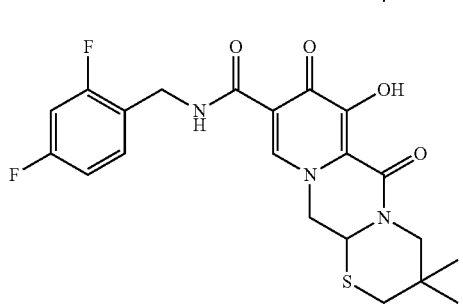
82
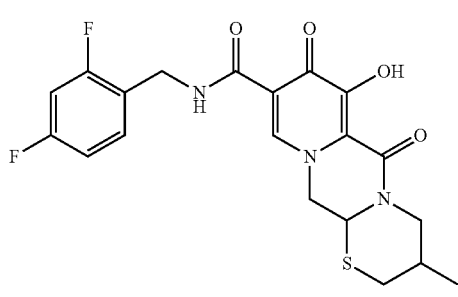
83
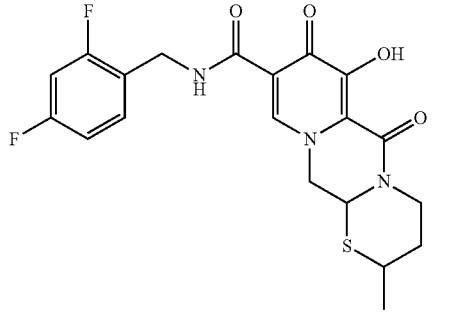
84
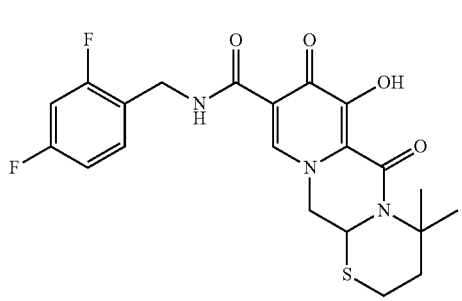

85
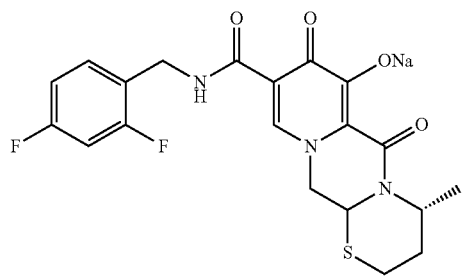

86
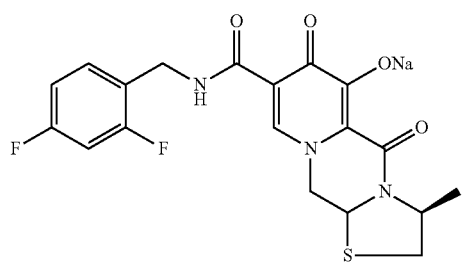

87
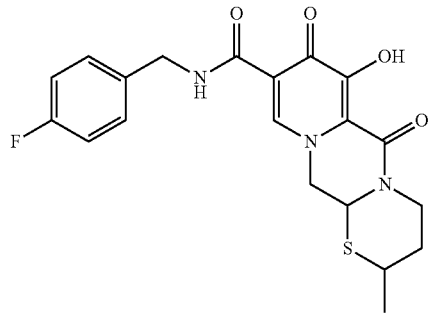

88
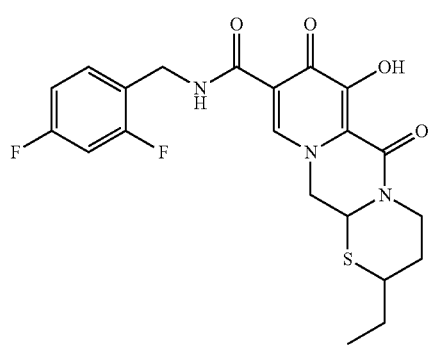

89
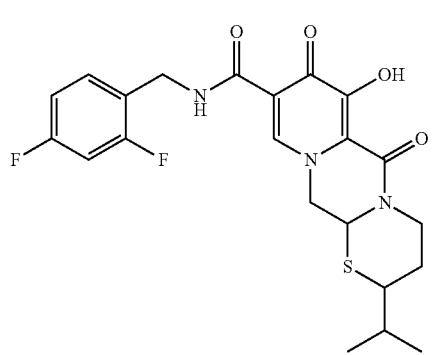

90
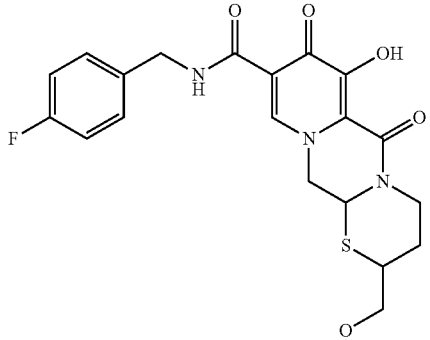

91
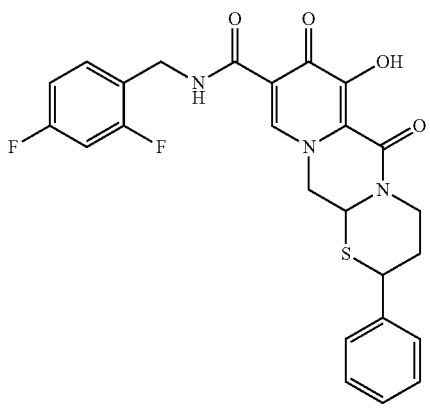

92
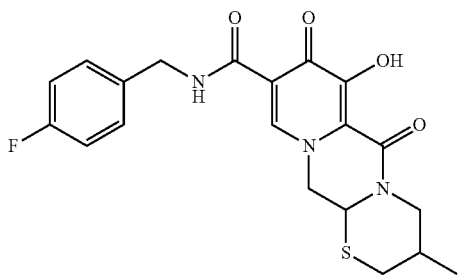

93
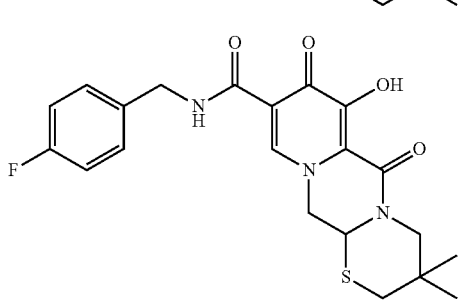

8. The compound according to claim 1, wherein the pharmaceutically acceptable salt is a sodium salt or a potassium salt.

9. A pharmaceutical composition, comprising a pharmaceutically acceptable carrier and the compound according to claim 1 or a pharmaceutically acceptable salt thereof as an active ingredient.

10. The pharmaceutical composition according to claim 9, the pharmaceutical composition further comprising one or more additional anti-HIV therapeutic agents.

11. A method for preparing the compound A3 according to claim 6, wherein the method is as follows:

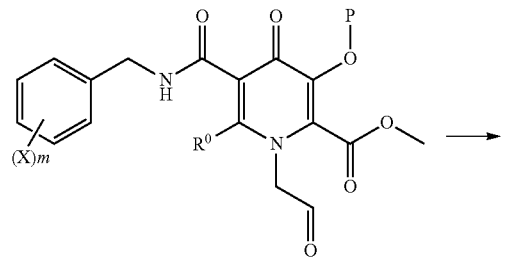
A1

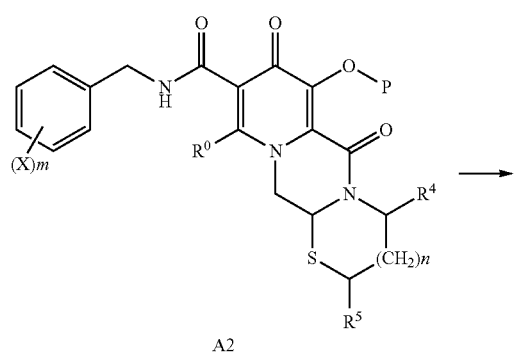
A2

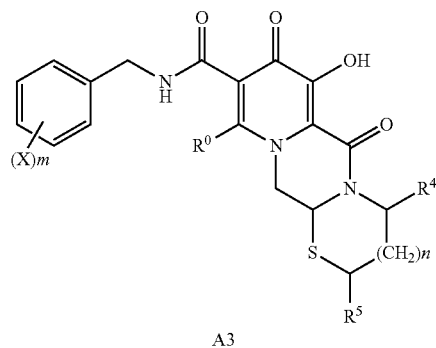
A3 the compound A1 and an aminothiol compound are heated and condensed under the catalysis of an acid to be converted into compound A2, and the protection group P of the compound A2 is removed to generate the compound A3.

12. A method for preparing the compound A3 according to claim 6, wherein the method is as follows:

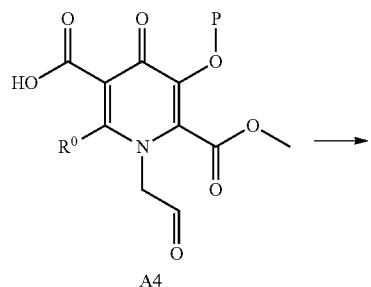
A4

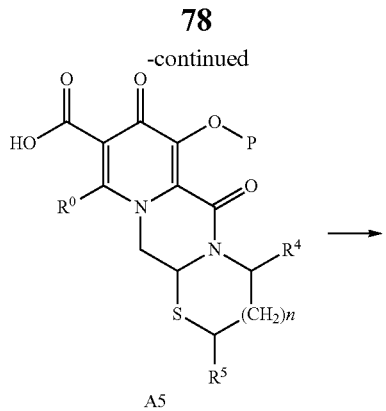
A5

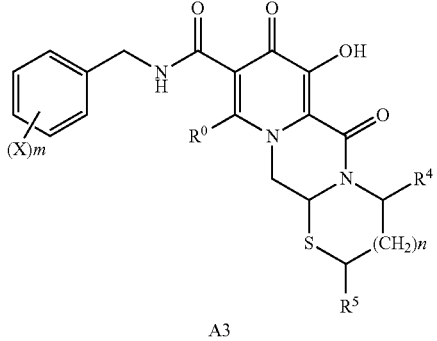
A3 the compound A4 and an aminothiol compound are heated and condensed under the catalysis of acid to generate compound A5; the compound A5 is converted into amide through amine and a coupling agent, and then the protection group P is removed to obtain the compound A3.

13. A method for preparing the compound A6 according to claim 6, wherein the method is as follows:

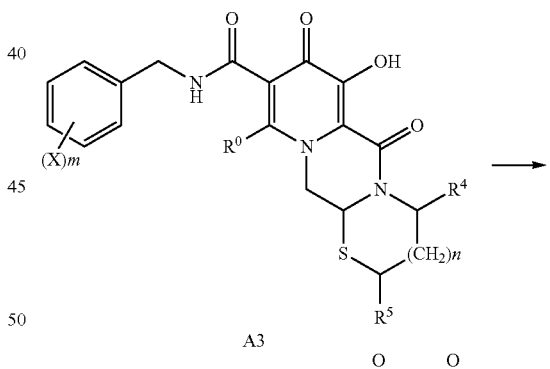
A3

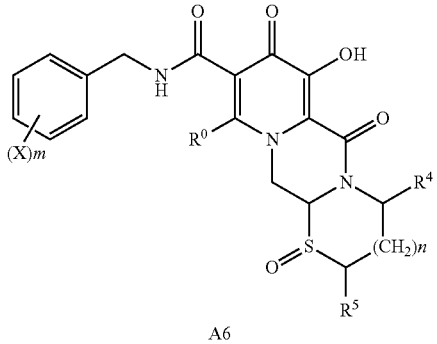
A6 the compound A3 is converted into the compound A6 by adding an oxidant.

14. A method for preparing the compound A7 according to claim 6, wherein the method is as follows:
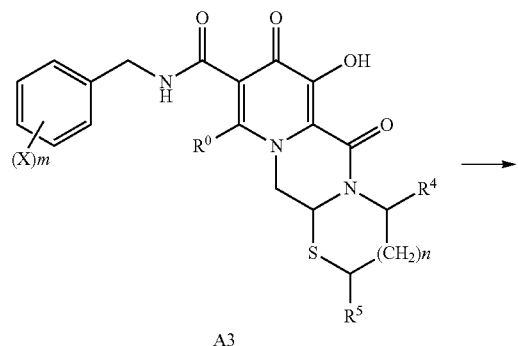
A3
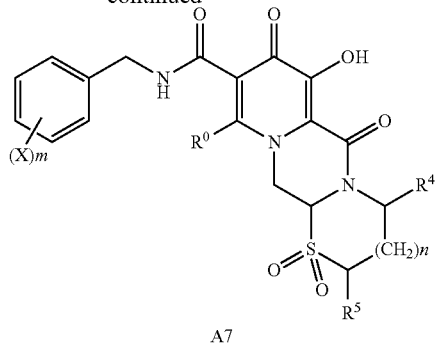
A7
the compound A3 is converted into the compound A7 by adding an oxidant.
* * * * *